(12) United States Patent
Wachendorff-Neumann et al.

(10) Patent No.: US 10,375,961 B2
(45) Date of Patent: Aug. 13, 2019

(54) ACTIVE COMPOUND COMBINATIONS CONTAINING A THIAZOYLISOXAZOLINE AND A FUNGICIDE

(71) Applicant: BAYER INTELLECTUAL PROPERTY GMBH, Monheim (DE)

(72) Inventors: Ulrike Wachendorff-Neumann, Neuwied (DE); Sebastian Hoffmann, Neuss (DE); Pierre Wasnaire, Duesseldorf (DE)

(73) Assignee: Bayer Intellectual Property GMBH, Monheim am Rhein (DE)

(*) Notice: Subject to any disclaimer, the term of this patent is extended or adjusted under 35 U.S.C. 154(b) by 0 days.

(21) Appl. No.: 15/421,946

(22) Filed: Feb. 1, 2017

(65) Prior Publication Data

US 2017/0142971 A1 May 25, 2017

Related U.S. Application Data

(62) Division of application No. 14/380,786, filed as application No. PCT/EP2013/053578 on Feb. 22, 2013, now Pat. No. 9,629,367.

(30) Foreign Application Priority Data

Feb. 27, 2012 (EP) ..................................... 12157090

(51) Int. Cl.

| A01N 43/80 | (2006.01) |
|---|---|
| A01N 57/12 | (2006.01) |
| A01N 25/00 | (2006.01) |
| A01N 37/34 | (2006.01) |
| A01N 43/38 | (2006.01) |
| A01N 43/40 | (2006.01) |
| A01N 43/54 | (2006.01) |
| A01N 43/56 | (2006.01) |
| A01N 43/90 | (2006.01) |
| A01N 47/08 | (2006.01) |
| A01N 47/28 | (2006.01) |
| A01N 37/20 | (2006.01) |
| A01N 37/38 | (2006.01) |
| A01N 37/42 | (2006.01) |
| A01N 37/46 | (2006.01) |
| A01N 37/50 | (2006.01) |
| A01N 43/50 | (2006.01) |
| A01N 43/88 | (2006.01) |
| A01N 45/02 | (2006.01) |
| A01N 47/04 | (2006.01) |
| A01N 47/12 | (2006.01) |
| A01N 47/14 | (2006.01) |
| A01N 47/24 | (2006.01) |
| A01N 47/34 | (2006.01) |
| A01N 59/02 | (2006.01) |
| A01N 59/20 | (2006.01) |
| A01N 59/26 | (2006.01) |
| A01N 43/653 | (2006.01) |

(52) U.S. Cl.
CPC ............. *A01N 43/80* (2013.01); *A01N 25/00* (2013.01); *A01N 37/34* (2013.01); *A01N 43/38* (2013.01); *A01N 43/40* (2013.01); *A01N 43/54* (2013.01); *A01N 43/56* (2013.01); *A01N 43/90* (2013.01); *A01N 47/08* (2013.01); *A01N 47/28* (2013.01); *A01N 57/12* (2013.01)

(58) Field of Classification Search
CPC combination set(s) only.
See application file for complete search history.

(56) References Cited

U.S. PATENT DOCUMENTS

| 4,139,616 A * | 2/1979 | Ducret ................... A01N 57/10 |
|---|---|---|
| | | 514/102 |
| 8,071,629 B2 | 12/2011 | Mansfield et al. |
| 8,449,898 B2 | 5/2013 | Gregory et al. |
| 8,524,743 B2 | 9/2013 | Cristau et al. |
| 2009/0099234 A1 | 4/2009 | Mansfield et al. |
| 2010/0240619 A1 | 9/2010 | Gregory et al. |
| 2014/0057945 A1 | 2/2014 | Cristau et al. |

FOREIGN PATENT DOCUMENTS

| CN | 101969781 A | 2/2011 |
|---|---|---|
| WO | 2006122955 A1 | 11/2006 |
| WO | 2007/079162 A1 | 7/2007 |
| WO | 2008013622 A2 | 1/2008 |
| WO | 2008013925 A2 | 1/2008 |
| WO | 2009055514 A2 | 4/2009 |

(Continued)

OTHER PUBLICATIONS

Aliette WDG label, Bayer CropScience LP, Research Triangle Park, NC (2011).*

(Continued)

*Primary Examiner* — John Pak

(74) *Attorney, Agent, or Firm* — McBee Moore Woodward & Vanik IP, LLC

(57) ABSTRACT

The present invention relates to active compound combinations, in particular within a fungicide composition, which comprises (A) a thiazolylisoxazoline of formula (I) and a further fungicidally active compound (B). Moreover, the invention relates to a method for curatively or preventively controlling the phytopathogenic fungi of plants or crops, to the use of a combination according to the invention for the treatment of seed, to a method for protecting a seed and not at least to the treated seed.

12 Claims, No Drawings

(56) References Cited

FOREIGN PATENT DOCUMENTS

| WO | 2009/080250 A2 | 7/2009 |
|---|---|---|
| WO | 2009094407 A2 | 7/2009 |
| WO | 2009094445 A2 | 7/2009 |
| WO | 2010065579 A2 | 6/2010 |
| WO | 2011/067272 A1 | 6/2011 |
| WO | 2011076699 A1 | 6/2011 |
| WO | 2011085170 A1 | 7/2011 |
| WO | WO 2012/02557 * 3/2012 | |

OTHER PUBLICATIONS

International Search Report from corresponding PCT/EP2013/053578, dated Jun. 6, 2013.
CABA abstract 2007:143100 (2007).
CABA abstract 2007:143130 (2007).
Leonard, Paul K., "Resistance risk evaluation, 'a European regulatory perspective," Crop Protection, vol. 19, pp. 905-909 (2000).
Issac, S., "What is the mode of actions of fungicides and how do fungi develop resistance?" Mycologist, vol. 13, Part 1, pp. 38-39 (Feb. 1999).

* cited by examiner

ACTIVE COMPOUND COMBINATIONS CONTAINING A THIAZOYLISOXAZOLINE AND A FUNGICIDE

CROSS REFERENCE TO RELATED APPLICATIONS

This application is a divisional application of U.S. application Ser. No. 14/380,768 (filed Aug. 25, 2014), which is a § 371 National Stage Application of PCT/EP2013/053578 (filed Feb. 22, 2013), which claims priority to EP 12157090.7 (filed Feb. 27, 2012), the contents of which are incorporated herein in their entireites.

BACKGROUND

Field of the Invention

The present invention relates to active compound combinations, in particular within a fungicide composition, which comprises (A) a thiazolylisoxazoline of formula (I) and a further fungicidally active compound (B). Moreover, the invention relates to a method for curatively or preventively controlling the phytopathogenic fungi of plants or crops, to the use of a combination according to the invention for the treatment of seed, to a method for protecting a seed and not at least to the treated seed.

Description of Related Art

It is already known that certain thiazolylisoxazolines can be used as fungicides (see WO2008/013925, WO2008/013622, WO2009/094407, WO2009/094445, WO2009/055514, WO2010/065579, WO2011/85170, and WO 2011/076699).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

The present invention provides active compound combinations/compositions which in some aspects at least achieve the stated objective.

SUMMARY

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the combination still achieves a high degree of phytopathogen control even where the two individual compounds have become totally ineffective in such a low application rate range. This allows, on the one hand, a substantial broadening of the spectrum of phytopathogens that can be controlled and, on the other hand, increased safety in use.

In addition to the fungicidal synergistic activity, the active compound combinations according to the invention have further surprising properties which, in a wider sense, may also be called synergistic, such as, for example: broadening of the activity spectrum to other phytopathogens, for example to resistant strains of plant diseases; lower application rates of the active compounds; sufficient control of pests with the aid of the active compound combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher persistency of the fungicidal action.

Accordingly, the present invention provides a combination comprising:
(A) at least one thiazolylisoxazoline of formula (I)

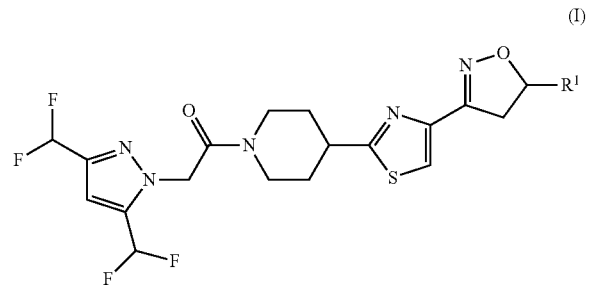

in which
R¹ represents phenyl, which is at least substituted with one methylsulfonyloxy and optionally be additionally substituted by one substituents selected from the group consisting of methyl, methoxy, fluoro or chloro,
or an agrochemically acceptable salt thereof,
and
(B) at least one further active compound selected from the following groups
  (1) inhibitors of the ergosterol synthesis,
  (2) inhibitors of the respiratory chain at complex I or II,
  (3) inhibitors of the respiratory chain at complex III,
  (4) inhibitors of the mitosis and cell division,
  (5) compounds capable of having a multisite action,
  (6) compounds capable of inducing a host defense,
  (7) inhibitors of the amino acid and/or protein biosynthesis,
  (8) inhibitors of the ATP production,
  (9) inhibitors of the cell wall synthesis,
  (10) inhibitors of the lipid and membrane synthesis,
  (11) inhibitors of the melanine biosynthesis,
  (12) inhibitors of the nucleic acid synthesis,

(13) inhibitors of the signal transduction,
(14) compounds capable of acting as uncoupler,
(15) other fungicides.

DETAILED DESCRIPTION OF A PREFERRED EMBODIMENT

Preference is given to combinations comprising at least one compound of the formula (I) selected from the group consisting of
(I-1) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}phenyl methanesulfonate,
(I-2) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-6-fluorophenyl methanesulfonate,
(I-3) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate,
(I-4) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-5-methylphenyl methanesulfonate,
(I-5) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-5-chlorophenyl methanesulfonate,
(I-6) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-4-methylphenyl methanesulfonate,
(I-7) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-4-chlorophenyl methanesulfonate,
(I-8) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-6-chlorophenyl methanesulfonate.

In the description below numbers in parenthesis behind a compound name represent the CAS Registry No. of said compound.

Preference is further given to combinations comprising at least one further active compound (B) selected from the following groups:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl -4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy] phenyl}imidoformamide, (1.64) O-[1-(4-methoxyphenoxy)-3,3-dimethylbutan-2-yl]1H-imidazole-l-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2,4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR, 9RS and anti-epimeric racemate 1RS,4SR,9SR) (881685-58-1), (2.12) isopyrazam (anti-epimeric racemate 1RS,4SR, 9SR), (2.13) isopyrazam (anti-epimeric enantiomer 1R,4S, 9S), (2.14) isopyrazam (anti-epimeric enantiomer 1S,4R, 9R), (2.15) isopyrazam (syn epimeric racemate 1RS,4SR, 9RS), (2.16) isopyrazam (syn-epimeric enantiomer 1R,4S, 9R), (2.17) isopyrazam (syn-epimeric enantiomer 1S,4R, 9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1, 1,2,2-tetrafluoroethoxy)phenyl]-3-(trifluoromethyl)-1H-pyrazole-4-carboxamide, (2.25) 3-(difluoromethyl)-1-methyl-N[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(tri-fluoromethyl)pyridin-2-yl]oxy}phenyl)ethyl]quinazolin-4-amine (1210070-84-0), (2.29) benzovindiflupyr, (2.30) N-[1(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(Difluor-methyl)-1-methyl-N-(1,1,3-trimethyl-2,3-dihydro-1H-inden-4-yl)-1H-pyrazol-4-carboxamid, (2.33) 1,3,5-Trimethyl-N-(1,1,3-trimethyl-2,3-dihydro-1H-inden-4-yl)-1H-pyrazol-4-carboxamid, (2.34) 1-Methyl-3-(trifluormethyl-N-(1,3,3-trimethyl-2,3-dihydro-1H-inden-4-yl)-1H-pyrazol-4-carboxamid, (2.35) 1-Methyl-3-(trifluormethyl)-N-[(1S)-1,3,3-trimethyl-2,3-dihydro-1H-inden-4-yl]-1H-pyrazol-4-carboxamid, (2.36) 1-Methyl-3-(trifluormethyl)-N-[(1R)-1,3,3-trimethyl-2,3-dihydro-1H-inden-4-yl]-1H-pyrazol-4-carboxamid, (2.37) 3-(Difluormethyl)-1-methyl-N-[(3S)-1,1,3-trimethyl-2,3-dihydro-1H-inden-4-yl]-1H-pyrazol-4-carboxamid, (2.38) 3-(Difluormethyl)-1-methyl-N-[(3R)-1,1,3-trimethyl-2,3-dihydro- 1H-inden-4-yl]-1H-pyrazol-4-carboxamid, (2.39) 1,3,5-Trimethyl-N-[(3R)-1,1,3-trimethyl-2,3-dihydro-1H-inden-4-yl]-1H-pyrazol-4-carboxamid, (2.40) 1,3,5-Trimethyl-N-[(3S)-1,1,3-trimethyl-2,3-dihydro-1H-inden-4-yl]-1H-pyrazol-4-carboxamid.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2), (3.9) famoxadone (131807-57-3), (3.10) fenamidone (161326-34-7), (3.11) fenoxystrobin (918162-02-4), (3.12) fluoxastrobin (361377-29-9), (3.13) kresoxim-methyl (143390-89-0), (3.14) metominostrobin (133408-50-1), (3.15) orysastrobin (189892-69-1), (3.16) picoxystrobin (117428-22-5), (3.17) pyraclostrobin (175013-18-0), (3.18) pyrametostrobin (915410-70-7), (3.19) pyraoxystrobin (862588-11-2), (3.20) pyribencarb (799247-52-2), (3.21) triclopyricarb (902760-40-1), (3.22) trifloxystrobin (141517-21-7), (3.23) (2E)-2-(2-{[6-(3-chloro-2-methyl-phenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy]imino)methyl]phenyl}ethanamide (158169-73-4), (3.26) (2E)-2-{2-[([(1E)-1-(3-{[(E)-1-fluoro-2-phenylethenyl]oxy}phenyl)ethyl-idene]amino]oxy)methyl]phenyl}-2-(methoxyimino)-N-ethylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methyl-ethanamide, (3.28) 2-chloro-N-(1,1,3-trimethyl-2,3-dihydro-1H-inden-4-yl)pyridine-3-carbox-amide (119899-14-8), (3.29) 5-methoxy-2-methyl-4-(2-[({(1E)-143-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfany)methyl]phenyl}-3-methoxyprop-2-enoate (149601-03-6), (3.31) N-(3-ethyl-3,5,5-trimethykyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0), (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluoro-phenyl)[1,2,4]triazolo[1,5-a]pyrimidine (214706-53-3), (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluoro-folpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4).

(6) Compounds capable to induce a host defence, like for example (6.1) acibenzolar-S-methyl (135158-54-2), (6.2) isotianil (224049-04-1), (6.3) probenazole (27605-76-1), (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0), (7.8) 3-(5-fluoro-3,3,4,4-tetramethyl-3,4-dihydroisoquinolin-1-yl)quinoline (861647-32-7).

(8) Inhibitors of the ATP production, for example (8.1) fentin acetate (900-95-8), (8.2) fentin chloride (639-58-7), (8.3) fentin hydroxide (76-87-9), (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8), (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0), (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2), (11.7) 2,2,2-trifluoroethyl 3-methyl-1-[(4-methylbenzoyl)amino]butan-2-yl}carbamate (851524-22-6).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3), (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7), (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6), (14.5) meptyldinocap (131-72-6).

(15) Further compounds, like for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5 -dioxonan-7-yl 2-methylpropanoate (517875-34-2), (15.54) 1-(4-{4-[(5R)-5-(2,6-difluorophenyl)-4,5-dihydro-1,2-oxazol-3-yl]-1,3-thiazo1-2-yl]piperidin-1-yl) -2-[5-methyl-3-(trifluoromethyl)-1H-pyrazol-1-yl] ethanone (1003319-79-6), (15.55) 1-(4-{44(5S)-5-(2,6-difluorophenyl)-4,5-dihydro-1,2-oxazol-3-1,3-thiazo1-2-yl] piperi-din-1-yl) -2-[5-methyl-3-(trifluoromethyl)-1H-pyrazol-1ethanone (1003319-80-9), (15.56) 1-(4-{4-[5-(2,6-difluorophenyl)-4,5-dihydro -1,2-oxazol-3-yl]-1,3-thiazo1-2-yl}piperidin-1-yl)-2[5-methyl-3-(trifluo-romethyl)-1H-pyrazol-1ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c'] dipyrrole-1,3,5,7(2,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl]piperidin-1 -yl) ethanone (1003316-53-7), (15.62) 245-methyl-3-(trifluoromethyl)-1H-pyrazol-1-yl]-1-(4-{4-[(5S)-5-phenyl-4,5-dihydro-1,2-oxazol-3-yl]-1,3-thiazo1-2-yl}piperidin-1-yl)ethanone (1003316-54-8), (15.63) 245-methyl-3-(trifluoromethyl)-1H-pyrazol-1-yl]-1-{444-(5-phenyl-4,5-dihydro-1,2-oxazol-3-yl)-1,3-thiazol-2-yl]piperidin-1-yl ethanone (1003316-51-5), (15.64) 2-butoxy-6-iodo-3-propyl-4H-chromen-4-one, (15.65) 2-chloro-542-chloro-1-(2, 6-difluoro-4-methoxyphenyl)-4-methyl-1H-imidazol-5-yl] pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0), (15.68) 3,4,5-trichloropyridine-2,6-dicarbonitrile (17824-85-0), (15.69) 345-(4-chlorophenyl)-2,3-dimethyl-1,2-oxazolidin-3-yl]pyridine, (15.70) 3-chloro-5-(4-chlorophenyl)-4-(2,6-difluorophenyl) -6-methylpyridazine, (15.71) 4-(4-chlorophenyl)-5-(2,6-difluorophenyl)-3,6-dimethylpyridazine, (15.72) 5-amino-1,3, 4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4), (15.75) 5-fluoro-2-[(4-methylbenzyl)oxy] pyrimidin-4-amine (1174376-25-0), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzy0-1,2,4-thiadiazol-5 oxy -2,5-dimethylphenyl)-N-ethyl-N-methylimidoformamide, (15.79) N-(4-chlorobenzyl)-343-methoxy-4-(prop-2-yn-1-yloxy)phenyl] propanamide, (15.80) N4(4-chlorophenyl)(cyano)methyl]-343-methoxy-4-(prop-2-yn-1-yloxy)phenyl]propanamide, (15.81) N4(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)4 (cyclopropylmethoxy)imino][6-(difluoromethoxy)-2,3-difluorophenyl]methyl}-2-phenylacetamide (221201-92-9), (15.85) N-(Z)-[(cyclopropylmethoxy)imino][6-(difluoromethoxy)-2,3-difluorophenyl]methyl -2-phenylacetamide (221201-92-9), (15.86) N'-{44(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl piperidin-4-yl)-N-(1,2,3,4-tetrahydronaphthalen -1-yl)-1,3-thiazole-4-carboxamide (922514-49-6), (15.88) N-methyl-2-(1-{[methyl-3-(trifluoromethyl)-1H-pyrazol-1-yl]acetyl }piperidin-4-yl)-N-[(1R)-1,2,3,4-tetrahydronaphthalen-1-yl]-1, 3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl {6[({[(1-methyl-1H-tetrazol-5-yl)(phenyl) methylidene]amino }oxy)methyl]pyridin-2-yl carbamate, (15.91) phenazine-1-carboxylic acid, (15.92) quinolin-8-ol (134-31-6), (15.93) quinolin-8-ol sulfate (2:1) (134-31-6), (15.94) tert-butyl {6-[({(([(1-methyl-1H-tetrazol-5-yl)(phenyl)methylene]amino}oxy)methyl]pyridin-2-yl carbamate.

(16) Further compounds, like for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl) biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4- carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide, (16.15) 4-(difluoromethyl)-2-methyl-N-[4'-(trifluoromethyl)bi-phenyl-2-yl]1,3-thiazole-5-carboxamide, (16.16) 5-fluoro-N-[4'-(3-hydroxy-3-methylbut-1-yn-1-yl)bi-phenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl) (2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid, (16.24) but-3-yn-1-yl64 ({[(Z)-(1-methyl-1H-tetrazol-5-yl)(phenyl)methylene]amino}oxy)methyl]pyridin-2-yl carbamate, (16.25) 4-Amino-5-fluorpyrimidin-2-ol (mesomere Form: 6-Amino-5-fluorpyrimidin-2(1H)-on), (16.26) propyl 3,4,5-trihydroxybenzoate.

All named mixing partners of the classes (1) to (16) can, if their functional groups enable this, optionally form salts with suitable bases or acids.

Particular preference is further given to combinations comprising at least one further active compound (B) selected from the following groups:

(2.1) bixafen, (2.2) boscalid, (2.6) fluopyram, (2.8) fluxapyroxad, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.27) N41 -(2,4-dichlorophenyl)-1-methoxypropan-2-yl]-3-(difluoromethyl)-1-methyl-1H-pyrazole-4-carboxamide, (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (3.1) ametoctradin, (3.2) amisulbrom, (3.3) azoxystrobin, (3.4) cyazofamid, (3.9) famoxadone, (3.10) fenamidone, (3.12) fluoxastrobin, (3.16) picoxystrobin, (3.17) pyraclostrobin, (3.22) trifloxystrobin, (4.6) fluopicolide, (5.1) bordeaux mixture, (5.4) chlorothalonil, (5.5) copper hydroxide, (5.7) copper oxide, (5.8) copper oxychloride, (5.9) copper(2+) sulfate, (5.16) folpet, (5.23) mancozeb, (5.25) metiram, (5.26) metiram zinc, (5.29) propineb, (5.30) sulphur and sulphur preparations including calcium polysulphide, (7.7) pyrimethanil, (9.2) dimethomorph, (9.4) iprovalicarb, (9.5) mandipropamid, (10.9) propamocarb, (10.10) propamocarb hydrochloride, (12.9) metalaxyl, (12.10) metalaxyl-M (mefenoxam), (14.4) fluazinam, (15.9) cymoxanil, (15.24) fosetyl-aluminium, (15.25) fosetyl-calcium, (15.26) fosetyl-sodium, (15.41) phosphorous acid and its salts, (15.42) propamocarb-fosetylate, (15.54) 1-(4-{4[(5R)-5-(2,6-difluorophenyl)-4,5-dihydro-1,2-oxazol-3-yl]-1,3-thiazol-2-yl}piperidin-1-yl)-2[5-methyl-3-(trifluoromethyl)-1H-pyrazol-1ethanone, (15.55) 1-(4-{[4(5S)-5-(2,6-difluorophenyl)-4,5-dihydro-1,2-oxazol-3-1,3-thiazol-2-yl]piperidin-1-yl) -2[5-methyl-3-(trifluoromethyl)-1H-pyrazol-1-yl]ethanone, (15.56) 1-(4-{4-[4-5-(2,6-difluorophenyl)-4,5-dihydro-1,2-oxazol-3-yl-1,3-thiazol-2-yl]piperidin-1-yl) -2-[5-methyl-3-(trifluoromethyl)-1H-pyrazol-1-yl]ethanone, (15.60) 2,6-dimethyl-1H,5H-[1,4]dithiino[2,3-c:5,6-c']dipyrrole-1,3,5,7(2H,6H)-tetrone, (15.90) pentyl {6-[({[(1-methyl-1H-tetrazol-5-yl)(phenyl)methylidene]amino}oxy)methyl]pyridin-2-yl }carbamate.

All named mixing partners of the classes (1) to (15) can, if their functional groups enable this, optionally form salts with suitable bases or acids.

In a preferred embodiment this invention is directed to mixtures comprising the compound (I-1) as compound of formula (I) and one component (B), in particular the mixtures (I-1)+(1.1), (I-1)+(1.2), (I-1)+(1.3), (I-1)+(1.4), (I-1)+(1.5), (I-1)+(1.6), (I-1)+(1.7), (I-1)+(1.8), (I-1)+(1.9), (I-1)+(1.10), (I-1)+(1.11), (I-1)+(1.12), (I-1)+(1.13), (I-1)+(1.14), (I-1)+(1.15), (I-1)+(1.16), (I-1)+(1.17), (I-1)+(1.18), (I-1)+(1.19), (I-1)+(1.20), (I-1)+(1.21), (I-1)+(1.22), (I-1)+(1.23), (I-1)+(1.24), (I-1)+(1.25), (I-1)+(1.26), (I-1)+(1.27), (I-1)+(1.28), (I-1)+(1.29), (I-1)+(1.30), (I-1)+(1.31), (I-1)+(1.32), (I-1)+(1.33), (I-1)+(1.34), (I-1)+(1.35), (I-1)+(1.36), (I-1)+(1.37), (I-1)+(1.38), (I-1)+(1.39), (I-1)+(1.40), (I-1)+(1.41), (I-1)+(1.42), (I-1)+(1.43), (I-1)+(1.44), (I-1)+(1.45), (I-1)+(1.46), (I-1)+(1.47), (I-1)+(1.48), (I-1)+(1.49), (I-1)+(1.50), (I-1)+(1.51), (I-1)+(1.52), (I-1)+(1.53), (I-1)+(1.54), (I-1)+(1.55), (I-1)+(1.56), (I-1)+(1.57), (I-1)+(1.58), (I-1)+(1.59), (I-1)+(1.60), (I-1)+(1.61), (I-1)+(1.62), (I-1)+(1.63), (I-1)+(1.64), (I-1)+(2.1), (I-1)+(2.2),(I-1)+(2.3), (I-1)+(2.4), (I-1)+(2.5), (I-1)+(2.6), (I-1)+(2.7), (I-1)+(2.8), (I-1)+(2.9), (I-1)+(2.10), (I-1)+(2.11), (I-1)+(2.12), (I-1)+(2.13), (I-1)+(2.14), (I-1)+(2.15), (I-1)+(2.16), (I-1)+(2.17), (I-1)+(2.18), (I-1)+(2.19), (I-1)+(2.20), (I-1)+(2.21), (I-1)+(2.22), (I-1)+(2.23), (I-1)+(2.24), (I-1)+(2.25), (I-1)+(2.26), (I-1)+(2.27), (I-1)+(2.28), (I-1)+(2.29), (I-1)+(3.1), (I-1)+(3.2), (I-1)+(3.3), (I-1)+(3.4), (I-1)+(3.5), (I-1)+(3.6), (I-1)+(3.7),(I-1)+(3.8), (I-1)+(3.9),(I-1)+(3.10), (I-1)+(3.11), (I-1)+(3.12), (I-1)+(3.13), (I-1)+(3.14), (I-1)+(3.15), (I-1)+(3.16), (I-1)+(3.17), (I-1)+(3.18), (I-1)+(3.19), (I-1)+(3.20), (I-1)+(3.21), (I-1)+(3.22), (I-1)+(3.23), (I-1)+(3.24), (I-1)+(3.25), (I-1)+(3.26), (I-1)+(3.27), (I-1)+(3.28), (I-1)+(3.29), (I-1)+(3.30), (I-1)+(3.31), (I-1)+(3.32), (I-1)+(3.33), (I-1)+(4.1), (I-1)+(4.2), (I-1)+(4.3), (I-1)+(4.4), (I-1)+(4.5), (I-1)+(4.6), (I-1)+(4.7), (I-1)+(4.8), (I-1)+(4.9), (I-1)+(4.10), (I-1)+(4.11), (I-1)+(4.12), (I-1)+(4.13), (I-1)+(4.14), (I-1)+(5.1), (I-1)+(5.2), (I-1)+(5.3), (I-1)+(5.4), (I-1)+(5.5), (I-1)+(5.6), (I-1)+(5.7), (I-1)+(5.8), (I-1)+(5.9), (I-1)+(5.10), (I-1)+(5.11), (I-1)+(5.12), (I-1)+(5.13), (I-1)+(5.14), (I-1)+(5.15), (I-1)+(5.16), (I-1)+(5.17), (I-1)+(5.18), (I-1)+(5.19), (I-1)+(5.20), (I-1)+(5.21), (I-1)+(5.22), (I-1)+(5.23), (I-1)+(5.24), (I-1)+(5.25), (I-1)+(5.26), (I-1)+(5.27), (I-1)+(5.28), (I-1)+(5.29), (I-1)+(5.30), (I-1)+(5.31), (I-1)+(5.32), (I-1)+(5.33), (I-1)+(5.34), (I-1)+(6.1), (I-1)+(6.2), (I-1)+(6.3), (I-1)+(6.4), (I-1)+(7.1), (I-1)+(7.2), (I-1)+(7.3), (I-1)+(7.4), (I-1)+(7.5), (I-1)+(7.6), (I-1)+(7.7), (I-1)+(7.8), (I-1)+(8.1), (I-1)+(8.2), (I-1)+(8.3), (I-1)+(8.4), (I-1)+(9.1), (I-1)+(9.2), (I-1)+(9.3), (I-1)+(9.4), (I-1)+(9.5), (I-1)+(9.6), (I-1)+(9.7),(I-1)+(9.8), (I-1)+(9.9),(I-1)+(10.1), (I-1)+(10.2), (I-1)+(10.3), (I-1)+(10.4), (I-1)+(10.5), (I-1)+(10.6), (I-1)+(10.7), (I-1)+(10.8), (I-1)+(10.9), (I-1)+(10.10), (I-1)+(10.11), (I-1)+(10.12), (I-1)+(10.13), (I-1)+(10.14), (I-1)+(10.15), (I-1)+(11.1), (I-1)+(11.2), (I-1)+(11.3), (I-1)+(11.4), (I-1)+(11.5), (I-1)+(11.6), (I-1)+(11.7), (I-1)+(12.1), (I-1)+(12.2), (I-1)+(12.3), (I-1)+(12.4), (I-1)+(12.5), (I-1)+(12.6), (I-1)+(12.7), (I-1)+(12.8), (I-1)+(12.9), (I-1)+(12.10), (I-1)+(12.11), (I-1)+(12.12), (I-1)+(12.13), (I-1)+(13.1), (I-1)+(13.2), (I-1)+(13.3), (I-1)+(13.4), (I-1)+(13.5), (I-1)+(13.6), (I-1)+(13.7), (I-1)+(14.1), (I-1)+(14.2), (I-1)+(14.3), (I-1)+(14.4), (I-1)+(14.5), (I-1)+(15.1), (I-1)+(15.2), (I-1)+(15.3), (I-1)+(15.4), (I-1)+(15.5), (I-1)+(15.6), (I-1)+(15.7), (I-1)+(15.8), (I-1)+(15.9), (I-1)+(15.10), (I-1)+(15.11), (I-1)+(15.12), (I-1)+(15.13), (I-1)+(15.14), (I-1)+(15.15), (I-1)+(15.16), (I-1)+(15.17), (I-1)+(15.18), (I-1)+(15.19), (I-1)+(15.20), (I-1)+(15.21), (I-1)+(15.22), (I-1)+(15.23), (I-1)+(15.24), (I-1)+(15.25), (I-1)+(15.26), (I-1)+(15.27), (I-1)+(15.28), (I-1)+(15.29), (I-1)+(15.30), (I-1)+(15.31), (I-1)+(15.32), (I-1)+(15.33), (I-1)+(15.34), (I-1)+(15.35), (I-1)+(15.36), (I-1)+(15.37), (I-1)+(15.38), (I-1)+(15.39), (I-1)+(15.41), (I-1)+(15.42), (I-1)+(15.43), (I-1)+(15.44), (I-1)+(15.45), (I-1)+(15.46), (I-1)+(15.47), (I-1)+(15.48), (I-1)+(15.49), (I-1)+(15.50), (I-1)+(15.51), (I-1)+(15.52), (I-1)+(15.53), (I-1)+(15.54), (I-1)+(15.55), (I-1)+(15.56), (I-1)+(15.57), (I-1)+(15.58), (I-1)+(15.59), (I-1)+(15.60), (I-1)+(15.61), (I-1)+(15.62), (I-1)+(15.63), (I-1)+(15.64), (I-1)+(15.65), (I-1)+(15.66), (I-1)+(15.67), (I-1)+(15.68), (I-1)+(15.69), (I-1)+(15.70), (I-1)+(15.71), (I-1)+(15.72), (I-1)+(15.73), (I-1)+(15.74), (I-1)+(15.75), (I-1)+(15.76), (I-1)+(15.77), (I-1)+(15.78), (I-1)+(15.79), (I-1)+(15.80), (I-1)+(15.81), (I-1)+(15.82), (I-1)+(15.83), (I-1)+(15.84), (I-1)+(15.85), (I-1)+(15.86), (I-1)+(15.87), (I-1)+(15.88), (I-1)+(15.89), (I-1)+(15.90), (I-1)+(15.91), (I-1)+(15.92), (I-1)+(15.93), (I-1)+(15.94).

In a further particularly preferred embodiment this invention is directed to mixtures comprising the compound (I-1) as compound of formula (I) and one component (B), in particular the mixtures (I-1)+(2.1), (I-1)+(2.2), (I-1)+(2.6), (I-1)+(2.8), (I-1)+(2.11), (I-1)+(2.12), (I-1)+(2.13), (I-1)+(2.14), (I-1)+(2.15), (I-1)+(2.16), (I-1)+(2.17), (I-1)+(2.29), (I-1)+(3.1), (I-1)+(3.2), (I-1)+(3.3), (I-1)+(3.4), (I-1)+(3.9), (I-1)+(3.10), (I-1)+(3.12), (I-1)+(3.16), (I-1)+(3.17), (I-1)+(3.22), (I-1)+(4.6), (I-1)+(5.1), (I-1)+(5.4), (I-1)+(5.5), (I-1)+(5.7), (I-1)+(5.8), (I-1)+(5.9), (I-1)+(5.16), (I-1)+(5.23), (I-1)+(5.25), (I-1)+(5.26), (I-1)+(5.29), (I-1)+(5.30), (I-1)+(7.7),(I-1)+(9.2),(I-1)+(9.4),(I-1)+(9.5),(I-1)+(10.9), (I-1)+(10.10), (I-1)+(12.9), (I-1)+(12.10), (I-1)+(14.4), (I-1)+(15.9), (I-1)+(15.24), (I-1)+(15.25), (I-1)+(15.26), (I-1)+(15.41), (I-1)+(15.42), (I-1)+(15.54), (I-1)+(15.55), (I-1)+(15.56), (I-1)+(15.60), (I-1)+(15.90).

In a preferred embodiment this invention is directed to mixtures comprising the compound (1-2) as compound of formula (I) and one component (B), in particular the mixtures (I-2)+(1.1), (I-2)+(1.2), (I-2)+(1.3), (I-2)+(1.4), (I-2)+(1.5), (I-2)+(1.6), (I-2)+(1.7), (I-2)+(1.8), (I-2)+(1.9), (I-2)+(1.10), (I-2)+(1.11(I-2)+(1.12), (I-2)+(1.13), (I-2)+(1.14), (I-2)+(1.15), (I-2)+(1.16), (I-2)+(1.17), (I-2)+(1.18), (I-2)+(1.19), (I-2)+(1.20), (I-2)+(1.21), (1-2)+(1.22), (1-2)+(1.23), (I-2)+(1.24), (I-2)+(1.25), (I-2)+(1.26), (I-2)+(1.27), (I-2)+(1.28), (1-2)+(1.29), (1-2)+(1.30), (I-2)+(1.31), (I-2)+(1.32), (I-2)+(1.33), (I-2)+(1.34), (I-2)+(1.35), (1-2)+(1.36), (1-2)+(1.37), (I-2)+(1.38), (I-2)+(1.39), (I-2)+(1.40), (I-2)+(1.41), (I-2)+(1.42), (1-2)+(1.43), (1-2)+(1.44), (1-2)+(1.45), (I-2)+(1.46), (I-2)+(1.47), (I-2)+(1.48), (I-2)+(1.49), (1-2)+(1.50), (1-2)+(1.51), (I-2)+(1.52), (I-2)+(1.53), (I-2)+(1.54), (I-2)+(1.55), (1-2)+(1.56), (1-2)+(1.57), (1-2)+(1.58), (1-2)+(1.59), (I-2)+(1.60), (I-2)+(1.61), (I-2)+(1.62), (I-2)+(1.63), (I-2)+(1.64), (I-2)+(2.1), (I-2)+(2.2), (I-2)+(2.3), (1-2)+(2.4), (I-2)+(2.5), (I-2)+(2.6), (I-2)+(2.7), (I-2)+(2.8), (I-2)+(2.9), (I-2)+(2.10), (I-2)+(2.11), (I-2)+(2.12), (I-2)+(2.13), (I-2)+(2.14), (I-2)+(2.15), (1-2)+(2.16), (I-2)+(2.17), (I-2)+(2.18), (I-2)+(2.19), (I-2)+(2.20), (I-2)+(2.21), (I-2)+(2.22), (1-2)+(2.23), (I-2)+(2.24), (I-2)+(2.25), (I-2)+(2.26), (I-2)+(2.27), (I-2)+(2.28), (I-2)+(2.29), (I-2)+(3.1), (I-2)+(3.2), (I-2)+(3.3), (I-2)+(3.4), (I-2)+(3.5), (I-2)+(3.6), (I-2)+(3.7), (I-2)+(3.8), (I-2)+(3.9), (I-2)+(3.10), (I-2)+(3.11), (I-2)+(3.12), (I-2)+(3.13), (I-2)+(3.14), (I-2)+(3.15), (I-2)+(3.16), (I-2)+(3.17), (I-2)+(3.18), (I-2)+(3.19), (I-2)+(3.20), (I-2)+(3.21), (I-2)+(3.22), (I-2)+(3.23), (I-2)+(3.24), (I-2)+(3.25), (I-2)+(3.26), (I-2)+(3.27), (I-2)+(3.28), (I-2)+(3.29), (I-2)+(3.30), (I-2)+(3.31), (I-2)+(3.32), (I-2)+(3.33), (I-2)+(4.1), (I-2)+(4.2), (I-2)+(4.3), (I-2)+(4.4), (I-2)+(4.5), (I-2)+(4.6), (I-2)+(4.7), (I-2)+(4.8), (I-2)+(4.9), (I-2)+(4.10), (I- 2)+(4.11), (I-2)+(4.12), (I-2)+(4.13), (I-2)+(4.14), (I-2)+(5.1), (I-2)+(5.2), (I-2)+(5.3), (I-2)+(5.4), (I-2)+(5.5), (I-2)+(5.6), (I-2)+(5.7), (I-2)+(5.8), (I-2)+(5.9), (I-2)+(5.10), (I-2)+(5.11), (I-2)+(5.12), (I-2)+(5.13), (I-2)+(5.14), (I-2)+(5.15), (I-2)+(5.16), (I-2)+(5.17), (I-2)+(5.18), (I-2)+(5.19), (I-2)+(5.20), (I-2)+(5.21), (I-2)+(5.22), (I-2)+(5.23), (I-2)+(5.24), (I-2)+(5.25), (I-2)+(5.26), (I-2)+(5.27), (I-2)+(5.28), (I-2)+(5.29), (I-2)+(5.30), (I-2)+(5.31), (I-2)+(5.32), (I-2)+(5.33), (I-2)+(5.34), (I-2)+(6.1), (I-2)+(6.2), (I-2)+(6.3), (I-2)+(6.4), (I-2)+(7.1), (I-2)+(7.2), (I-2)+(7.3), (I-2)+(7.4), (I-2)+(7.5), (I-2)+(7.6), (I-2)+(7.7), (I-2)+(7.8), (I-2)+(8.1), (I-2)+(8.2), (I-2)+(8.3), (I-2)+(8.4), (I-2)+(9.1), (I-2)+(9.2), (I-2)+(9.3), (I-2)+(9.4), (I-2)+(9.5), (I-2)+(9.6), (I-2)+(9.7), (I-2)+(9.8), (I-2)+(9.9), (I-2)+(10.1), (I-2)+(10.2), (I-2)+(10.3), (10.4), (I-2)+(10.5), (I-2)+(10.6), (I-2)+(10.7), (I-2)+(10.8), (I-2)+(10.9), (I-2)+(10.10), (I-2)+(10.11), (I-2)+(10.12), (I-2)+(10.13), (I-2)+(10.14), (I-2)+(10.15), (I-2)+(11.1), (I-2)+(11.2), (I-2)+(11.3), (I-2)+(11.4), (I-2)+(11.5), (I-2)+(11.6), (I-2)+(11.7), (I-2)+(12.1), (I-2)+(12.2), (I-2)+(12.3), (I-2)+(12.4), (I-2)+(12.5), (I-2)+(12.6), (I-2)+(12.7), (I-2)+(12.8), (I-2)+(12.9), (I-2)+(12.10), (I-2)+(12.11), (I-2)+(12.12), (I-2)+(12.13), (I-2)+(13.1), (I-2)+(13.2), (I-2)+(13.3), (I-2)+(13.4), (I-2)+(13.5), (I-2)+(13.6), (I-2)+(13.7), (I-2)+(14.1), (I-2)+(14.2), (I-2)+(14.3), (I-2)+(14.4), (I-2)+(14.5), (I-2)+(15.1), (I-2)+(15.2), (I-2)+(15.3), (I-2)+(15.4), (I-2)+(15.5), (I-2)+(15.6), (I-2)+(15.7), (I-2)+(15.8), (I-2)+(15.9), (I-2)+(15.10), (I-2)+(15.11), (I-2)+(15.12), (I-2)+(15.13), (I-2)+(15.14), (I-2)+(15.15), (I-2)+(15.16), (I-2)+(15.17), (I-2)+(15.18), (I-2)+(15.19), (I-2)+(15.20), (I-2)+(15.21), (I-2)+(15.22), (I-2)+(15.23), (I-2)+(15.24), (I-2)+(15.25), (I-2)+(15.26), (I-2)+(15.27), (I-2)+(15.28), (I-2)+(15.29), (I-2)+(15.30), (I-2)+(15.31), (I-2)+(15.32), (I-2)+(15.33), (I-2)+(15.34), (I-2)+(15.35), (I-2)+(15.36), (I-2)+(15.37), (I-2)+(15.38), (I-2)+(15.39), (I-2)+(15.41), (I-2)+(15.42), (I-2)+(15.43), (I-2)+(15.44), (I-2)+(15.45), (I-2)+(15.46), (I-2)+(15.47), (I-2)+(15.48), (I-2)+(15.49), (I-2)+(15.50), (I-2)+(15.51), (I-2)+(15.52), (I-2)+(15.53), (I-2)+(15.54), (I-2)+(15.55), (I-2)+(15.56), (I-2)+(15.57), (I-2)+(15.58), (I-2)+(15.59), (I-2)+(15.60), (I-2)+(15.61), (I-2)+(15.62), (I-2)+(15.63), (I-2)+(15.64), (I-2)+(15.65), (I-2)+(15.66), (I-2)+(15.67), (I-2)+(15.68), (I-2)+(15.69), (I-2)+(15.70), (I-2)+(15.71), (I-2)+(15.72), (I-2)+(15.73), (I-2)+(15.74), (I-2)+(15.75), (I-2)+(15.76), (I-2)+(15.77), (I-2)+(15.78), (I-2)+(15.79), (I-2)+(15.80), (I-2)+(15.81), (I-2)+(15.82), (I-2)+(15.83), (I-2)+(15.84), (I-2)+(15.85), (I-2)+(15.86), (I-2)+(15.87), (I-2)+(15.88), (I-2)+(15.89), (I-2)+(15.90), (I-2)+(15.91), (I-2)+(15.92), (I-2)+(15.93), (I-2)+(15.94).

In a further particularly preferred embodiment this invention is directed to mixtures comprising the compound (I-2) as compound of formula (I) and one component (B), in particular the mixtures (I-2)+(2.1), (I-2)+(2.2), (I-2)+(2.6), (I-2)+(2.8), (I-2)+(2.11), (I-2)+(2.12), (I-2)+(2.13), (I-2)+(2.14), (I-2)+(2.15), (I-2)+(2.16), (I-2)+(2.17), (I-2)+(2.29), (I-2)+(3.1), (I-2)+(3.2), (I-2)+(3.3), (I-2)+(3.4),(I-2)+(3.9), (I-2)+(3.10), (I-2)+(3.12), (I-2)+(3.16), (I-2)+(3.17), (I-2)+

(3.22), (I-2)+(4.6), (I-2)+(5.1), (I-2)+(5.4), (I-2)+(5.5),(I-2)+(5.7),(I-2)+(5.8),(I-2)+(5.9),(I-2)+(5.16), (I-2)+(5.23), (I-2)+(5.25), (I-2)+(5.26), (I-2)+(5.29), (I-2)+(5.30), (I-2)+(7.7), (I-2)+(9.2), (I-2)+(9.4), (I-2)+(9.5), (I-2)+(10.9), (I-2)+(10.10), (I-2)+(12.9), (I-2)+(12.10), (I-2)+(14.4), (I-2)+(15.9), (I-2)+(15.24), (I-2)+(15.25), (I-2)+(15.26), (I-2)+(15.41), (I-2)+(15.42), (I-2)+(15.54), (I-2)+(15.55), (I-2)+(15.56), (I-2)+(15.60), (I-2)+(15.90).

In a preferred embodiment this invention is directed to mixtures comprising the compound (I-3) as compound of formula (I) and one component (B), in particular the mixtures (I-3)+(1.1), (I-3)+(1.2), (I-3)+(1.3), (I-3)+(1.4), (I-3)+(1.5), (I-3)+(1.6), (I-3)+(1.7), (I-3)+(1.8), (I-3)+(1.9), (I-3)+(1.10), (I-3)+(1.11), (I-3)+(1.12), (I-3)+(1.13), (I-3)+(1.14), (I-3)+(1.15), (I-3)+(1.16), (I-3)+(1.17), (I-3)+(1.18), (I-3)+(1.19), (I-3)+(1.20), (I-3)+(1.21), (I-3)+(1.22), (I-3)+(1.23), (I-3)+(1.24), (I-3)+(1.25), (I-3)+(1.26), (I-3)+(1.27), (I-3)+(1.28), (I-3)+(1.29), (I-3)+(1.30), (I-3)+(1.31), (I-3)+(1.32), (I-3)+(1.33), (I-3)+(1.34), (I-3)+(1.35), (I-3)+(1.36), (I-3)+(1.37), (I-3)+(1.38), (I-3)+(1.39), (I-3)+(1.40), (I-3)+(1.41), (I-3)+(1.42), (I-3)+(1.43), (I-3)+(1.44), (I-3)+(1.45), (I-3)+(1.46), (I-3)+(1.47), (I-3)+(1.48), (I-3)+(1.49), (I-3)+(1.50), (I-3)+(1.51), (I-3)+(1.52), (I-3)+(1.53), (I-3)+(1.54), (I-3)+(1.55), (I-3)+(1.56), (I-3)+(1.57), (I-3)+(1.58), (I-3)+(1.59), (I-3)+(1.60), (I-3)+(1.61), (I-3)+(1.62), (I-3)+(1.63), (I-3)+(1.64), (I-3)+(2.1), (I-3)+(2.2), (I-3)+(2.3), (I-3)+(2.4), (I-3)+(2.5), (I-3)+(2.6), (I-3)+(2.7), (I-3)+(2.8), (I-3)+(2.9), (I-3)+(2.10), (I-3)+(2.11), (I-3)+(2.12), (I-3)+(2.13), (I-3)+(2.14), (I-3)+(2.15), (I-3)+(2.16), (I-3)+(2.17), (I-3)+(2.18), (I-3)+(2.19), (I-3)+(2.20), (I-3)+(2.21), (I-3)+(2.22), (1-3)+(2.23), (1-3)+(2.24), (I-3)+(2.25), (I-3)+(2.26), (I-3)+(2.27), (I-3)+(2.28), (I-3)+(2.29), (I-3)+(3.1), (I-3)+(3.2), (I-3)+(3.3), (1-3)+(3.4), (I-3)+(3.5), (I-3)+(3.6),(I-3)+(3.7),(I-3)+(3.8),(I-3)+(3.9),(I-3)+(3.10), (I-3)+(3.11), (I-3)+(3.12), (I-3)+(3.13), (I-3)+(3.14), (I-3)+(3.15), (I-3)+(3.16), (I-3)+(3.17), (I-3)+(3.18), (I-3)+(3.19), (I-3)+(3.20), (I-3)+(3.21), (I-3)+(3.22), (I-3)+(3.23), (I-3)+(3.24), (I-3)+(3.25), (I-3)+(3.26), (I-3)+(3.27), (I-3)+(3.28), (I-3)+(3.29), (I-3)+(3.30), (I-3)+(3.31), (I-3)+(3.32), (I-3)+(3.33), (I-3)+(4.1),(I-3)+(4.2), (I-3)+(4.3), (I-3)+(4.4),(I-3)+(4.5), (I-3)+(4.6), (I-3)+(4.7), (I-3)+(4.8), (I-3)+(4.9), (I-3)+(4.10), (I-3)+(4.11), (I-3)+(4.12), (I-3)+(4.13), (I-3)+(4.14), (I-3)+(5.1), (I-3)+(5.2), (I-3)+(5.3), (I-3)+(5.4), (I-3)+(5.5), (I-3)+(5.6),(I-3)+(5.7), (I-3)+(5.8),(I-3)+(5.9), (I-3)+(5.10), (I-3)+(5.11), (I-3)+(5.12), (I-3)+(5.13), (I-3)+(5.14), (I-3)+(5.15), (I-3)+(5.16), (I-3)+(5.17), (I-3)+(5.18), (I-3)+(5.19), (I-3)+(5.20), (I-3)+(5.21), (I-3)+(5.22), (I-3)+(5.23), (I-3)+(5.24), (I-3)+(5.25), (I-3)+(5.26), (I-3)+(5.27), (I-3)+(5.28), (I-3)+(5.29), (I-3)+(5.30), (I-3)+(5.31), (I-3)+(5.32), (I-3)+(5.33), (I-3)+(5.34), (I-3)+(6.1), (I-3)+(6.2), (I-3)+(6.3), (I-3)+(6.4), (I-3)+(7.1), (I-3)+(7.2), (I-3)+(7.3), (I-3)+(7.4), (I-3)+(7.5), (I-3)+(7.6), (I-3)+(7.7), (I-3)+(7.8), (I-3)+(8.1), (I-3)+(8.2), (I-3)+(8.3), (I-3)+(8.4), (I-3)+(9.1), (I-3)+(9.2), (I-3)+(9.3), (I-3)+(9.4), (I-3)+(9.5), (I-3)+(9.6), (I-3)+(9.7), (I-3)+(9.8), (I-3)+(9.9), (I-3)+(10.1), (I-3)+(10.2), (I-3)+(10.3), (I-3)+(10.4), (I-3)+(10.5), (I-3)+(10.6), (I-3)+(10.7), (I-3)+(10.8), (I-3)+(10.9), (I-3)+(10.10), (I-3)+(10.11), (I-3)+(10.12), (I-3)+(10.13), (I-3)+(10.14), (I-3)+(10.15), (I-3)+(11.1), (I-3)+(11.2), (I-3)+(11.3), (I-3)+(11.4), (I-3)+(11.5), (I-3)+(11.6), (I-3)+(11.7), (I-3)+(12.1), (I-3)+(12.2), (I-3)+(12.3), (I-3)+(12.4), (I-3)+(12.5), (I-3)+(12.6), (I-3)+(12.7), (I-3)+(12.8), (I-3)+(12.9), (I-3)+(12.10), (I-3)+(12.11), (I-3)+(12.12), (I-3)+(12.13), (I-3)+(13.1), (I-3)+(13.2), (I-3)+(13.3), (I-3)+(13.4), (I-3)+(13.5), (I-3)+(13.6), (I-3)+(13.7), (I-3)+(14.1), (I-3)+(14.2), (I-3)+(14.3), (I-3)+(14.4), (I-3)+(14.5), (I-3)+(15.1), (I-3)+(15.2), (I-3)+(15.3), (I-3)+(15.4), (I-3)+(15.5), (I-3)+(15.6), (I-3)+(15.7), (I-3)+(15.8), (I-3)+(15.9), (I-3)+(15.10), (I-3)+(15.11), (I-3)+(15.12), (I-3)+(15.13), (I-3)+(15.14), (I-3)+(15.15), (I-3)+(15.16), (I-3)+(15.17), (I-3)+(15.18), (I-3)+(15.19), (I-3)+(15.20), (I-3)+(15.21), (I-3)+(15.22), (I-3)+(15.23), (I-3)+(15.24), (I-3)+(15.25), (I-3)+(15.26), (I-3)+(15.27), (I-3)+(15.28), (I-3)+(15.29), (I-3)+(15.30), (I-3)+(15.31), (I-3)+(15.32), (I-3)+(15.33), (I-3)+(15.34), (I-3)+(15.35), (I-3)+(15.36), (I-3)+(15.37), (I-3)+(15.38), (I-3)+(15.39), (I-3)+(15.41), (I-3)+(15.42), (I-3)+(15.43), (I-3)+(15.44), (I-3)+(15.45), (I-3)+(15.46), (I-3)+(15.47), (I-3)+(15.48), (I-3)+(15.49), (I-3)+(15.50), (I-3)+(15.51), (I-3)+(15.52), (I-3)+(15.53), (I-3)+(15.54), (I-3)+(15.55), (I-3)+(15.56), (I-3)+(15.57), (I-3)+(15.58), (I-3)+(15.59), (I-3)+(15.60), (I-3)+(15.61), (I-3)+(15.62), (I-3)+(15.63), (I-3)+(15.64), (I-3)+(15.65), (I-3)+(15.66), (I-3)+(15.67), (I-3)+(15.68), (I-3)+(15.69), (I-3)+(15.70), (I-3)+(15.71), (I-3)+(15.72), (I-3)+(15.73), (I-3)+(15.74), (I-3)+(15.75), (I-3)+(15.76), (I-3)+(15.77), (I-3)+(15.78), (I-3)+(15.79), (I-3)+(15.80), (I-3)+(15.81), (I-3)+(15.82), (I-3)+(15.83), (I-3)+(15.84), (I-3)+(15.85), (I-3)+(15.86), (I-3)+(15.87), (I-3)+(15.88), (I-3)+(15.89), (I-3)+(15.90), (I-3)+(15.91), (I-3)+(15.92), (I-3)+(15.93), (I-3)+(15.94).

In a further particularly preferred embodiment this invention is directed to mixtures comprising the compound (I-3) as compound of formula (I) and one component (B), in particular the mixtures (I-3)+(2.1), (I-3)+(2.2), (I-3)+(2.6), (I-3)+(2.8), (I-3)+(2.11), (I-3)+(2.12), (I-3)+(2.13), (I-3)+(2.14), (I-3)+(2.15), (I-3)+(2.16), (I-3)+(2.17), (I-3)+(2.29), (I-3)+(3.1), (I-3)+(3.2), (I-3)+(3.3), (1-3)+(3.4), (I-3)+(3.9), (I-3)+(3.10), (I-3)+(3.12), (I-3)+(3.16), (1-3)+(3.17), (I-3)+(3.22), (I-3)+(4.6), (I-3)+(5.1), (I-3)+(5.4), (I-3)+(5.5),(I-3)+(5.7), (I-3)+(5.8),(I-3)+(5.9),(I-3)+(5.16), (I-3)+(5.23), (I-3)+(5.25), (I-3)+(5.26), (I-3)+(5.29), (I-3)+(5.30), (I-3)+(7.7), (I-3)+(9.2), (I-3)+(9.4), (I-3)+(9.5), (I-3)+(10.9), (I-3)+(10.10), (I-3)+(12.9), (I-3)+(12.10), (I-3)+(14.4), (I-3)+(15.9), (I-3)+(15.24), (I-3)+(15.25), (I-3)+(15.26), (I-3)+(15.41), (I-3)+(15.42), (1-3)+(15.54), (1-3)+(15.55), (I-3)+(15.56), (I-3)+(15.60), (I-3)+(15.90).

In a preferred embodiment this invention is directed to mixtures comprising the compound (1-4) as compound of formula (I) and one component (B), in particular the mixtures (I-4)+(1.1), (I-4)+(1.2), (I-4)+(1.3), (I-4)+(1.4), (I-4)+(1.5), (I-4)+(1.6), (I-4)+(1.7), (I-4)+(1.8), (I-4)+(1.9), (I-4)+(1.10), (1-4)+(1.11), (I- 4)+(1.12), (I-4-)+(1.13), (I-4)+(1.14), (I-4)+(1.15), (I-4)+(1.16), (I-4)+(1.17), (I-4)+(1.18), (I-4)+(1.19), (I-4)+(1.20), (I-4)+(1.21), (1-4)+(1.22), (I-4)+(1.23), (I-4)+(1.24), (I-4)+(1.25), (I-4)+(1.26), (I-4)+(1.27), (I-4)+(1.28), (1-4)+(1.29), (1-4)+(1.30), (I-4)+(1.31), (I-4)+(1.32), (I-4)+(1.33), (I-4)+(1.34), (I-4)+(1.35), (1-4)+(1.36), (1-4)+(1.37), (I-4)+(1.38), (I-4)+(1.39), (I-4)+(1.40), (I-4)+(1.41), (I-4)+(1.42), (1-4)+(1.43), (I-4)+(1.44), (I-4)+(1.45), (I-4)+(1.46), (I-4)+(1.47), (I-4)+(1.48), (I-4)+(1.49), (I-4)+(1.50), (I-4)+(1.51), (I-4)+(1.52), (I-4)+(1.53), (I-4)+(1.54), (I-4)+(1.55), (I-4)+(1.56), (I-4)+(1.57), (I-4)+(1.58), (I-4)+(1.59), (I-4)+(1.60), (I-4)+(1.61), (I-4)+(1.62), (I-4)+(1.63), (I-4)+(1.64), (I-4)+(2.1), (I-4)+(2.2), (I-4)+(2.3), (1-4)+(2.4), (I-4)+(2.5), (I-4)+(2.6), (I-4)+(2.7), (I-4)+(2.8), (I-4)+(2.9), (I-4)+(2.10), (I-4)+(2.11), (I-4)+(2.12), (I-4)+(2.13), (I-4-)+(2.14), (I-4)+(2.15), (1-4)+(2.16), (I-4)+(2.17), (I-4)+(2.18), (I-4)+(2.19), (I-4)+(2.20), (I-4-)+(2.21), (I-4)+(2.22), (1-4)+(2.23), (I-4)+(2.24), (I-4)+(2.25), (I-4)+(2.26), (I-4)+(2.27), (I-4)+(2.28), (I-4)+(2.29), (I-4)+(3.1), (1-4)+(3.2), (I-4)+(3.3), (1-4)+(3.4), (1-4)+(3.5), (I-4)+(3.6),(I-4)+(3.7), (I-4)+(3.8), (I-4)+(3.9), (1-4)+(3.10), (I-4)+(3.11), (I-4)+(3.12), (I-4)+(3.13), (I- 4)+(3.14), (I-4)+(3.15), (I-4)+(3.16), (I-4)+(3.17), (I-4)+(3.18), (I-4)+(3.19), (I-4)+(3.20), (I-4)+(3.21), (I-4-)+(3.22), (I-4)+(3.23), (1-4)+(3.24), (I-4)+

(3.25), (I-4)+(3.26), (I-4)+(3.27), (I-4)+(3.28), (I-4)+(3.29), (I-4)+(3.30), (I-4)+(3.31), (I-4)+(3.32), (I-4)+(3.33), (I-4)+(4.1), (I-4)+(4.2), (I-4)+(4.3), (I-4)+(4.4),(I-4)+(4.5), (I-4)+(4.6), (I-4)+(4.7), (I-4)+(4.8), (I-4)+(4.9), (I-4)+(4.10), (I-4)+(4.11), (I-4)+(4.12), (I-4)+(4.13), (I-4)+(4.14), (I-4)+(5.1), (I-4)+(5.2), (I-4)+(5.3), (I-4)+(5.4), (I-4)+(5.5), (I-4)+(5.6),(I-4)+(5.7), (I-4)+(5.8),(I-4)+(5.9), (I-4)+(5.10), (I-4)+(5.11), (I-4)+(5.12), (I- 4)+(5.13), (I-4-)+(5.14), (I-4)+(5.15), (1-4)+(5.16), (I-4)+(5.17), (I-4)+(5.18), (I-4)+(5.19), (I-4)+(5.20), (I-4)+(5.21), (I-4)+(5.22), (I-4)+(5.23), (I-4)+(5.24), (I-4)+(5.25), (I-4)+(5.26), (I-4)+(5.27), (I-4)+(5.28), (I-4)+(5.29), (I-4)+(5.30), (I-4)+(5.31), (I-4)+(5.32), (I-4)+(5.33), (I-4)+(5.34), (I-4)+(6.1), (I-4)+(6.2), (I-4)+(6.3), (I-4)+(6.4), (I-4)+(7.1), (I-4)+(7.2), (I-4)+(7.3), (I-4)+(7.4), (I-4)+(7.5), (I-4)+(7.6), (I-4)+(7.7), (I-4)+(7.8), (I-4)+(8.1), (I-4)+(8.2), (I-4)+(8.3), (I-4)+(8.4), (I-4)+(9.1), (I-4)+(9.2), (I-4)+(9.3), (I-4)+(9.4), (I-4)+(9.5), (I-4)+(9.6), (I-4)+(9.7), (I-4)+(9.8), (I-4)+(9.9), (I-4)+(10.1), (I-4)+(10.2), (I-4)+(10.3), (I-4)+(10.4), (I-4)+(10.5), (I-4)+(10.6), (I-4)+(10.7), (I-4)+(10.8), (I-4)+(10.9), (I-4)+(10.10), (I-4)+(10.11), (I-4)+(10.12), (I-4)+(10.13), (I-4)+(10.14), (I-4)+(10.15), (I-4)+(11.1), (I-4)+(11.2), (I-4)+(11.3), (I-4)+(11.4), (I-4)+(11.5), (I-4)+(11.6), (I-4)+(11.7), (I-4)+(12.1), (I-4)+(12.2), (I-4)+(12.3), (I-4)+(12.4), (I-4)+(12.5), (I-4)+(12.6), (I-4)+(12.7), (I-4)+(12.8), (I-4)+(12.9), (I-4)+(12.10), (I-4)+(12.11), (I-4)+(12.12), (I-4)+(12.13), (I-4)+(13.1), (I-4)+(13.2), (I-4)+(13.3), (I-4)+(13.4), (I-4)+(13.5), (I-4)+(13.6), (I-4)+(13.7), (I-4)+(14.1), (I-4)+(14.2), (I-4)+(14.3), (I-4)+(14.4), (I-4)+(14.5), (I-4)+(15.1), (I-4)+(15.2), (I-4)+(15.3), (I-4)+(15.4), (I-4)+(15.5), (I-4)+(15.6), (I-4)+(15.7), (I-4)+(15.8), (I-4)+(15.9), (I-4)+(15.10), (I-4)+(15.11), (I-4)+(15.12), (I-4)+(15.13), (I-4)+(15.14), (I-4)+(15.15), (I-4)+(15.16), (I-4)+(15.17), (I-4)+(15.18), (I-4)+(15.19), (I-4)+(15.20), (I-4)+(15.21), (I-4)+(15.22), (I-4)+(15.23), (I-4)+(15.24), (I-4)+(15.25), (I-4)+(15.26), (I-4)+(15.27), (I-4)+(15.28), (I-4)+(15.29), (I-4)+(15.30), (I-4-)+(15.31), (I-4)+(15.32), (I-4)+(15.33), (I-4)+(15.34), (I-4)+(15.35), (I-4)+(15.36), (I-4)+(15.37), (I-4)+(15.38), (I-4)+(15.39), (I-4)+(15.41), (I-4)+(15.42), (I-4)+(15.43), (I-4)+(15.44), (I-4)+(15.45), (I-4)+(15.46), (I-4)+(15.47), (I-4)+(15.48), (I-4)+(15.49), (I-4)+(15.50), (I-4)+(15.51), (I-4)+(15.52), (I-4)+(15.53), (I-4)+(15.54), (I-4)+(15.55), (I-4)+(15.56), (I-4)+(15.57), (I-4)+(15.58), (I-4)+(15.59), (I-4)+(15.60), (I-4)+(15.61), (I-4)+(15.62), (I-4)+(15.63), (I-4)+(15.64), (I-4)+(15.65), (I-4)+(15.66), (I-4-)+(15.67), (I-4)+(15.68), (I-4)+(15.69), (I-4)+(15.70), (I-4)+(15.71), (I-4)+(15.72), (I-4)+(15.73), (I-4)+(15.74), (I-4)+(15.75), (I-4)+(15.76), (I-4)+(15.77), (I-4)+(15.78), (I-4)+(15.79), (I-4)+(15.80), (I-4)+(15.81), (I-4)+(15.82), (I-4)+(15.83), (I-4)+(15.84), (I-4)+(15.85), (I-4)+(15.86), (I-4)+(15.87), (I-4)+(15.88), (I-4)+(15.89), (I-4)+(15.90), (I-4)+(15.91), (I-4)+(15.92), (I-4)+(15.93), (I-4)+(15.94).

In a further particularly preferred embodiment this invention is directed to mixtures comprising the compound (I-4) as compound of formula (I) and one component (B), in particular the mixtures (I-4)+(2.1), (I-4)+(2.2), (I-4)+(2.6), (I-4)+(2.8), (I-4)+(2.11), (I-4)+(2.12), (I-4)+(2.13), (I-4)+(2.14), (I-4)+(2.15), (I-4)+(2.16), (I-4)+(2.17), (I-4)+(2.29), (I-4)+(3.1), (I-4)+(3.2), (I-4)+(3.3), (I-4)+(3.4),(I-4)+(3.9), (I-4)+(3.10), (I-4)+(3.12), (I-4)+(3.16), (I-4)+(3.17), (I-4)+(3.22), (I-4)+(4.6), (I-4)+(5.1), (I-4)+(5.4), (I-4)+(5.5),(I-4)+(5.7),(I-4)+(5.8),(I-4)+(5.9),(I-4)+(5.16), (I-4)+(5.23), (I-4)+(5.25), (I-4)+(5.26), (I-4)+(5.29), (I-4)+(5.30), (I-4)+(7.7), (I-4)+(9.2), (I-4)+(9.4), (I-4)+(9.5), (I-4)+(10.9), (I-4)+(10.10), (I-4)+(12.9), (I-4)+(12.10), (I-4)+(14.4), (I-4)+(15.9), (I-4)+(15.24), (I-4)+(15.25), (I-4)+(15.26), (I-4)+(15.41), (I-4)+(15.42), (I-4)+(15.54), (I-4)+(15.55), (I-4)+(15.56), (I-4)+(15.60), (I-4)+(15.90).

In a preferred embodiment this invention is directed to mixtures comprising the compound (I-5) as compound of formula (I) and one component (B), in particular the mixtures (I-5)+(1.1), (I-5)+(1.2), (I-5)+(1.3), (I-5)+(1.4), (I-5)+(1.5), (I-5)+(1.6), (I-5)+(1.7), (I-5)+(1.8), (I-5)+(1.9), (I-5)+(1.10), (I-5)+(1.11), (I-5)+(1.12), (I-5)+(1.13), (I-5)+(1.14), (I-5)+(1.15), (I-5)+(1.16), (I-5)+(1.17), (I-5)+(1.18), (I-5)+(1.19), (I-5)+(1.20), (I-5)+(1.21), (I-5)+(1.22), (I-5)+(1.23), (I-5)+(1.24), (I-5)+(1.25), (I-5)+(1.26), (I-5)+(1.27), (I-5)+(1.28), (I-5)+(1.29), (I-5)+(1.30), (I-5)+(1.31), (I-5)+(1.32), (I-5)+(1.33), (I-5)+(1.34), (I-5)+(1.35), (I-5)+(1.36), (I-5)+(1.37), (I-5)+(1.38), (I-5)+(1.39), (I-5)+(1.40), (I-5)+(1.41), (I-5)+(1.42), (I-5)+(1.43), (I-5)+(1.44), (I-5)+(1.45), (I-5)+(1.46), (I-5)+(1.47), (I-5)+(1.48), (I-5)+(1.49), (I-5)+(1.50), (I-5)+(1.51), (I-5)+(1.52), (I-5)+(1.53), (I-5)+(1.54), (I-5)+(1.55), (I-5)+(1.56), (I-5)+(1.57), (I-5)+(1.58), (I-5)+(1.59), (I-5)+(1.60), (I-5)+(1.61), (I-5)+(1.62), (I-5)+(1.63), (I-5)+(1.64), (I-5)+(2.1), (I-5)+(2.2), (I-5)+(2.3), (I-5)+(2.4), (I-5)+(2.5), (I-5)+(2.6), (I-5)+(2.7), (I-5)+(2.8), (I-5)+(2.9), (I-5)+(2.10), (I-5)+(2.11), (I-5)+(2.12), (I-5)+(2.13), (I-5)+(2.14), (I-5)+(2.15), (I-5)+(2.16), (I-5)+(2.17), (I-5)+(2.18), (I-5)+(2.19), (I-5)+(2.20), (I-5)+(2.21), (I-5)+(2.22), (1-5)+(2.23), (1-5)+(2.24), (I-5)+(2.25), (I-5)+(2.26), (I-5)+(2.27), (I-5)+(2.28), (I-5)+(2.29), (I-5)+(3.1), (I-5)+(3.2), (I-5)+(3.3), (I-5)+(3.4), (I-5)+(3.5), (I-5)+(3.6), (I-5)+(3.7), (I-5)+(3.8), (I-5)+(3.9), (I-5)+(3.10), (I-5)+(3.11), (I-5)+(3.12), (I-5)+(3.13), (I-5)+(3.14), (I-5)+(3.15), (I-5)+(3.16), (I-5)+(3.17), (I-5)+(3.18), (I-5)+(3.19), (I-5)+(3.20), (I-5)+(3.21), (I-5)+(3.22), (I-5)+(3.23), (I-5)+(3.24), (I-5)+(3.25), (I-5)+(3.26), (I-5)+(3.27), (I-5)+(3.28), (I-5)+(3.29), (I-5)+(3.30), (I-5)+(3.31), (I-5)+(3.32), (I-5)+(3.33), (I-5)+(4.1),(I-5)+(4.2), (I-5)+(4.3), (I-5)+(4.4), (I-5)+(4.5), (I-5)+(4.6), (I-5)+(4.7), (I-5)+(4.8), (I-5)+(4.9), (I-5)+(4.10), (I- 5)+(4.11), (I-5)+(4.12), (I-5)+(4.13), (I-5)+(4.14), (I-5)+(5.1), (I-5)+(5.2), (I-5)+(5.3), (I-5)+(5.4), (I-5)+(5.5), (I-5)+(5.6),(I-5)+(5.7), (I-5)+(5.8),(I-5)+(5.9), (I-5)+(5.10), (I-5)+(5.11), (I-5)+(5.12), (I-5)+(5.13), (I-5)+(5.14), (I-5)+(5.15), (I-5)+(5.16), (I-5)+(5.17), (I-5)+(5.18), (I-5)+(5.19), (I-5)+(5.20), (I-5)+(5.21), (I-5)+(5.22), (I-5)+(5.23), (I-5)+(5.24), (I-5)+(5.25), (I-5)+(5.26), (I-5)+(5.27), (I-5)+(5.28), (I-5)+(5.29), (I-5)+(5.30), (I-5)+(5.31), (I-5)+(5.32), (I-5)+(5.33), (I-5)+(5.34), (I-5)+(6.1), (I-5)+(6.2), (I-5)+(6.3), (I-5)+(6.4), (I-5)+(7.1), (I-5)+(7.2), (I-5)+(7.3), (I-5)+(7.4), (I-5)+(7.5), (I-5)+(7.6), (I-5)+(7.7), (I-5)+(7.8), (I-5)+(8.1), (I-5)+(8.2), (I-5)+(8.3), (I-5)+(8.4), (I-5)+(9.1), (I-5)+(9.2), (I-5)+(9.3), (I-5)+(9.4), (I-5)+(9.5), (I-5)+(9.6), (I-5)+(9.7), (I-5)+(9.8), (I-5)+(9.9), (I-5)+(10.1), (I-5)+(10.2), (I-5)+(10.3), (I-5)+(10.4), (I-5)+(10.5), (I-5)+(10.6), (I-5)+(10.7), (I-5)+(10.8), (I-5)+(10.9), (I-5)+(10.10), (I-5)+(10.11), (I-5)+(10.12), (I-5)+(10.13), (I-5)+(10.14), (I-5)+(10.15), (I-5)+(11.1), (I-5)+(11.2), (I-5)+(11.3), (I-5)+(11.4), (I-5)+(11.5), (I-5)+(11.6), (I-5)+(11.7), (I-5)+(12.1), (I-5)+(12.2), (I-5)+(12.3), (I-5)+(12.4), (I-5)+(12.5), (I-5)+(12.6), (I-5)+(12.7), (I-5)+(12.8), (I-5)+(12.9), (I-5)+(12.10), (I-5)+(12.11), (I-5)+(12.12), (I-5)+(12.13), (I-5)+(13.1), (I-5)+(13.2), (I-5)+(13.3), (I-5)+(13.4), (I-5)+(13.5), (I-5)+(13.6), (I-5)+(13.7), (I-5)+(14.1), (I-5)+(14.2), (I-5)+(14.3), (I-5)+(14.4), (I-5)+(14.5), (I-5)+(15.1), (I-5)+(15.2), (I-5)+(15.3), (I-5)+(15.4), (I-5)+(15.5), (I-5)+(15.6), (I-5)+(15.7), (I-5)+(15.8), (I-5)+(15.9), (I-5)+(15.10), (I-5)+(15.11), (I-5)+(15.12), (I-5)+(15.13), (I-5)+(15.14), (I-5)+(15.15), (I-5)+(15.16), (I-5)+(15.17), (I-5)+(15.18), (I-5)+(15.19), (I-5)+(15.20), (I-5)+(15.21), (I-5)+(15.22), (I-5)+(15.23), (I-5)+(15.24), (I-5)+(15.25), (I-5)+(15.26), (I-5)+(15.27), (I-5)+(15.28), (I-5)+(15.29), (I-5)+(15.30), (I-5)+(15.31), (I-5)+(15.32), (I-5)+

(15.33), (I-5)+(15.34), (I-5)+(15.35), (I-5)+(15.36), (I-5)+(15.37), (I-5)+(15.38), (I-5)+(15.39), (I-5)+(15.41), (I-5)+(15.42), (I-5)+(15.43), (I-5)+(15.44), (I-5)+(15.45), (I-5)+(15.46), (I-5)+(15.47), (I-5)+(15.48), (I-5)+(15.49), (I-5)+(15.50), (I-5)+(15.51), (I-5)+(15.52), (I-5)+(15.53), (I-5)+(15.54), (I-5)+(15.55), (I-5)+(15.56), (I-5)+(15.57), (I-5)+(15.58), (I-5)+(15.59), (I-5)+(15.60), (I-5)+(15.61), (I-5)+(15.62), (I-5)+(15.63), (I-5)+(15.64), (I-5)+(15.65), (I-5)+(15.66), (I-5)+(15.67), (I-5)+(15.68), (I-5)+(15.69), (I-5)+(15.70), (I-5)+(15.71), (I-5)+(15.72), (I-5)+(15.73), (I-5)+(15.74), (I-5)+(15.75), (I-5)+(15.76), (I-5)+(15.77), (I-5)+(15.78), (I-5)+(15.79), (I-5)+(15.80), (I-5)+(15.81), (I-5)+(15.82), (I-5)+(15.83), (I-5)+(15.84), (I-5)+(15.85), (I-5)+(15.86), (I-5)+(15.87), (I-5)+(15.88), (I-5)+(15.89), (I-5)+(15.90), (I-5)+(15.91), (I-5)+(15.92), (I-5)+(15.93), (I-5)+(15.94).

In a further particularly preferred embodiment this invention is directed to mixtures comprising the compound (I-5) as compound of formula (I) and one component (B), in particular the mixtures (I-5)+(2.1), (I-5)+(2.2), (I-5)+(2.6), (I-5)+(2.8), (I-5)+(2.11), (I-5)+(2.12), (I-5)+(2.13), (I-5)+(2.14), (I-5)+(2.15), (I-5)+(2.16), (I-5)+(2.17), (I-5)+(2.29), (I-5)+(3.1), (I-5)+(3.2), (I-5)+(3.3), (I-5)+(3.4), (I-5)+(3.9), (I-5)+(3.10), (I-5)+(3.12), (I-5)+(3.16), (I-5)+(3.17), (I-5)+(3.22), (I-5)+(4.6), (I-5)+(5.1), (I-5)+(5.4), (I-5)+(5.5), (I-5)+(5.7), (I-5)+(5.8), (I-5)+(5.9), (I-5)+(5.16), (I-5)+(5.23), (I-5)+(5.25), (I-5)+(5.26), (I-5)+(5.29), (I-5)+(5.30), (I-5)+(7.7), (I-5)+(9.2), (I-5)+(9.4), (I-5)+(9.5), (I-5)+(10.9), (I-5)+(10.10), (I-5)+(12.9), (I-5)+(12.10), (I-5)+(14.4), (I-5)+(15.9), (I-5)+(15.24), (I-5)+(15.25), (I-5)+(15.26), (I-5)+(15.41), (I-5)+(15.42), (I-5)+(15.54), (I-5)+(15.55), (I-5)+(15.56), (I-5)+(15.60), (I-5)+(15.90).

In a preferred embodiment this invention is directed to mixtures comprising the compound (I-6) as compound of formula (I) and one component (B), in particular the mixtures (I-6)+(1.1), (I-6)+(1.2), (I-6)+(1.3), (I-6)+(1.4), (I-6)+(1.5), (I-6)+(1.6), (I-6)+(1.7), (I-6)+(1.8), (I-6)+(1.9), (I-6)+(1.10), (I-6)+(1.11), (I-6)+(1.12), (I-6)+(1.13), (I-6)+(1.14), (I-6)+(1.15), (I-6)+(1.16), (I-6)+(1.17), (I-6)+(1.18), (I-6)+(1.19), (I-6)+(1.20), (I-6)+(1.21), (I-6)+(1.22), (I-6)+(1.23), (I-6)+(1.24), (I-6)+(1.25), (I-6)+(1.26), (I-6)+(1.27), (I-6)+(1.28), (I-6)+(1.29), (I-6)+(1.30), (I-6)+(1.31), (I-6)+(1.32), (I-6)+(1.33), (I-6)+(1.34), (I-6)+(1.35), (I-6)+(1.36), (I-6)+(1.37), (I-6)+(1.38), (I-6)+(1.39), (I-6)+(1.40), (I-6)+(1.41), (I-6)+(1.42), (I-6)+(1.43), (I-6)+(1.44), (I-6)+(1.45), (I-6)+(1.46), (I-6)+(1.47), (I-6)+(1.48), (I-6)+(1.49), (I-6)+(1.50), (I-6)+(1.51), (I-6)+(1.52), (I-6)+(1.53), (I-6)+(1.54), (I-6)+(1.55), (I-6)+(1.56), (I-6)+(1.57), (I-6)+(1.58), (I-6)+(1.59), (I-6)+(1.60), (I-6)+(1.61), (I-6)+(1.62), (I-6)+(1.63), (I-6)+(1.64), (I-6)+(2.1), (I-6)+(2.2), (I-6)+(2.3), (I-6)+(2.4), (I-6)+(2.5), (I-6)+(2.6), (I-6)+(2.7), (I-6)+(2.8), (I-6)+(2.9), (I-6)+(2.10), (I-6)+(2.11), (I-6)+(2.12), (I-6)+(2.13), (I-6)+(2.14), (I-6)+(2.15), (I-6)+(2.16), (I-6)+(2.17), (I-6)+(2.18), (I-6)+(2.19), (I-6)+(2.20), (I-6)+(2.21), (I-6)+(2.22), (I-6)+(2.23), (I-6)+(2.24), (I-6)+(2.25), (I-6)+(2.26), (I-6)+(2.27), (I-6)+(2.28), (I-6)+(2.29), (I-6)+(3.1), (I-6)+(3.2), (I-6)+(3.3), (I-6)+(3.4), (I-6)+(3.5), (I-6)+(3.6),(I-6)+(3.7),(I-6)+(3.8),(I-6)+(3.9), (I-6)+(3.10), (I-6)+(3.11), (I-6)+(3.12), (I-6)+(3.13), (I-6)+(3.14), (I-6)+(3.15), (I-6)+(3.16), (I-6)+(3.17), (I-6)+(3.18), (I-6)+(3.19), (I-6)+(3.20), (I-6)+(3.21), (I-6)+(3.22), (I-6)+(3.23), (I-6)+(3.24), (I-6)+(3.25), (I-6)+(3.26), (I-6)+(3.27), (I-6)+(3.28), (I-6)+(3.29), (I-6)+(3.30), (I-6)+(3.31), (I-6)+(3.32), (I-6)+(3.33), (I-6)+(4.1), (I-6)+(4.2), (I-6)+(4.3), (I-6)+(4.4),(I-6)+(4.5), (I-6)+(4.6), (I-6)+(4.7), (I-6)+(4.8), (I-6)+(4.9), (I-6)+(4.10), (I-6)+(4.11), (I-6)+(4.12), (I-6)+(4.13), (I-6)+(4.14), (I-6)+(5.1), (I-6)+(5.2), (I-6)+(5.3), (I-6)+(5.4), (I-6)+(5.5), (I-6)+(5.6),(I-6)+(5.7), (I-6)+(5.8),(I-6)+(5.9), (1-6)+(5.10), (I-6)+(5.11), (I-6)+(5.12), (I-6)+(5.13), (I-6)+(5.14), (I-6)+(5.15), (1-6)+(5.16), (I-6)+(5.17), (I-6)+(5.18), (I-6)+(5.19), (I-6)+(5.20), (I-6)+(5.21), (I-6)+(5.22), (I-6)+(5.23), (I-6)+(5.24), (I-6)+(5.25), (I-6)+(5.26), (I-6)+(5.27), (I-6)+(5.28), (I-6)+(5.29), (I-6)+(5.30), (I-6)+(5.31), (I-6)+(5.32), (I-6)+(5.33), (I-6)+(5.34), (I-6)+(6.1), (I-6)+(6.2), (I-6)+(6.3), (I-6)+(6.4), (I-6)+(7.1), (I-6)+(7.2), (I-6)+(7.3), (I-6)+(7.4), (I-6)+(7.5), (I-6)+(7.6), (I-6)+(7.7), (I-6)+(7.8), (I-6)+(8.1), (I-6)+(8.2), (I-6)+(8.3), (I-6)+(8.4), (I-6)+(9.1), (I-6)+(9.2), (I-6)+(9.3), (I-6)+(9.4), (I-6)+(9.5), (I-6)+(9.6), (I-6)+(9.7), (I-6)+(9.8), (I-6)+(9.9), (I-6)+(10.1), (I-6)+(10.2), (I-6)+(10.3), (I-6)+(10.4), (I-6)+(10.5), (I-6)+(10.6), (I-6)+(10.7), (I-6)+(10.8), (I-6)+(10.9), (I-6)+(10.10), (I-6)+(10.11), (I-6)+(10.12), (I-6)+(10.13), (I-6)+(10.14), (I-6)+(10.15), (I-6)+(11.1), (I-6)+(11.2), (I-6)+(11.3), (I-6)+(11.4), (I-6)+(11.5), (I-6)+(11.6), (I-6)+(11.7), (I-6)+(12.1), (I-6)+(12.2), (I-6)+(12.3), (I-6)+(12.4), (I-6)+(12.5), (I-6)+(12.6), (I-6)+(12.7), (I-6)+(12.8), (I-6)+(12.9), (I-6)+(12.10), (I-6)+(12.11), (I-6)+(12.12), (I-6)+(12.13), (I-6)+(13.1), (I-6)+(13.2), (I-6)+(13.3), (I-6)+(13.4), (I-6)+(13.5), (I-6)+(13.6), (I-6)+(13.7), (I-6)+(14.1), (I-6)+(14.2), (I-6)+(14.3), (I-6)+(14.4), (I-6)+(14.5), (I-6)+(15.1), (I-6)+(15.2), (I-6)+(15.3), (I-6)+(15.4), (I-6)+(15.5), (I-6)+(15.6), (I-6)+(15.7), (I-6)+(15.8), (I-6)+(15.9), (I-6)+(15.10), (I-6)+(15.11), (I-6)+(15.12), (I-6)+(15.13), (I-6)+(15.14), (I-6)+(15.15), (I-6)+(15.16), (I-6)+(15.17), (I-6)+(15.18), (I-6)+(15.19), (I-6)+(15.20), (I-6)+(15.21), (I-6)+(15.22), (I-6)+(15.23), (I-6)+(15.24), (I-6)+(15.25), (I-6)+(15.26), (I-6)+(15.27), (I-6)+(15.28), (I-6)+(15.29), (I-6)+(15.30), (I-6)+(15.31), (I-6)+(15.32), (I-6)+(15.33), (I-6)+(15.34), (I-6)+(15.35), (I-6)+(15.36), (I-6)+(15.37), (I-6)+(15.38), (I-6)+(15.39), (I-6)+(15.41), (I-6)+(15.42), (I-6)+(15.43), (I-6)+(15.44), (I-6)+(15.45), (I-6)+(15.46), (I-6)+(15.47), (I-6)+(15.48), (I-6)+(15.49), (I-6)+(15.50), (I-6)+(15.51), (I-6)+(15.52), (I-6)+(15.53), (I-6)+(15.54), (I-6)+(15.55), (I-6)+(15.56), (I-6)+(15.57), (I-6)+(15.58), (I-6)+(15.59), (I-6)+(15.60), (I-6)+(15.61), (I-6)+(15.62), (I-6)+(15.63), (I-6)+(15.64), (I-6)+(15.65), (I-6)+(15.66), (I-6)+(15.67), (I-6)+(15.68), (I-6)+(15.69), (I-6)+(15.70), (I-6)+(15.71), (I-6)+(15.72), (I-6)+(15.73), (I-6)+(15.74), (I-6)+(15.75), (I-6)+(15.76), (I-6)+(15.77), (I-6)+(15.78), (I-6)+(15.79), (I-6)+(15.80), (I-6)+(15.81), (I-6)+(15.82), (I-6)+(15.83), (I-6)+(15.84), (I-6)+(15.85), (I-6)+(15.86), (I-6)+(15.87), (I-6)+(15.88), (I-6)+(15.89), (I-6)+(15.90), (I-6)+(15.91), (I-6)+(15.92), (I-6)+(15.93), (I-6)+(15.94).

In a further particularly preferred embodiment this invention is directed to mixtures comprising the compound (I-6) as compound of formula (I) and one component (B), in particular the mixtures (I-6)+(2.1), (I-6)+(2.2), (I-6)+(2.6), (I-6)+(2.8), (I-6)+(2.11), (I-6)+(2.12), (I-6)+(2.13), (I-6)+(2.14), (I-6)+(2.15), (I-6)+(2.16), (I-6)+(2.17), (I-6)+(2.29), (I-6)+(3.1), (I-6)+(3.2), (I-6)+(3.3), (I-6)+(3.4), (I-6)+(3.9), (I-6)+(3.10), (I-6)+(3.12), (I-6)+(3.16), (I-6)+(3.17), (I-6)+(3.22), (I-6)+(4.6), (I-6)+(5.1), (I-6)+(5.4), (I-6)+(5.5),(I-6)+(5.7),(I-6)+(5.8),(I-6)+(5.9),(I-6)+(5.16), (I-6)+(5.23), (I-6)+(5.25), (I-6)+(5.26), (I-6)+(5.29), (I-6)+(5.30), (I-6)+(7.7), (I-6)+(9.2), (I-6)+(9.4), (I-6)+(9.5), (I-6)+(10.9), (I-6)+(10.10), (I-6)+(12.9), (I-6)+(12.10), (I-6)+(14.4), (I-6)+(15.9), (I-6)+(15.24), (I-6)+(15.25), (I-6)+(15.26), (I-6)+(15.41), (I-6)+(15.42), (I-6)+(15.54), (I-6)+(15.55), (I-6)+(15.56), (I-6)+(15.60), (I-6)+(15.90).

In a preferred embodiment this invention is directed to mixtures comprising the compound (I-7) as compound of formula (I) and one component (B), in particular the mixtures (I-7)+(1.1), (I-7)+(1.2), (I-7)+(1.3), (I-7)+(1.4), (I-7)+(1.5), (I-7)+(1.6), (I-7)+(1.7), (I-7)+(1.8), (I-7)+(1.9), (I-7)+

(1.10), (I-7)+(1.11), (I-7)+(1.12), (I-7)+(1.13), (I-7)+(1.14), (I-7)+(1.15), (I-7)+(1.16), (I-7)+(1.17), (I-7)+(1.18), (I-7)+(1.19), (I-7)+(1.20), (I-7)+(1.21), (I-7)+(1.22), (I-7)+(1.23), (I-7)+(1.24), (I-7)+(1.25), (I-7)+(1.26), (I-7)+(1.27), (I-7)+(1.28), (I-7)+(1.29), (I-7)+(1.30), (I-7)+(1.31), (I-7)+(1.32), (I-7)+(1.33), (I-7)+(1.34), (I-7)+(1.35), (I-7)+(1.36), (I-7)+(1.37), (I-7)+(1.38), (I-7)+(1.39), (I-7)+(1.40), (I-7)+(1.41), (I-7)+(1.42), (I-7)+(1.43), (I-7)+(1.44), (I-7)+(1.45), (I-7)+(1.46), (I-7)+(1.47), (I-7)+(1.48), (I-7)+(1.49), (I-7)+(1.50), (I-7)+(1.51), (I-7)+(1.52), (I-7)+(1.53), (I-7)+(1.54), (I-7)+(1.55), (I-7)+(1.56), (I-7)+(1.57), (I-7)+(1.58), (I-7)+(1.59), (I-7)+(1.60), (I-7)+(1.61), (I-7)+(1.62), (I-7)+(1.63), (I-7)+(1.64), (I-7)+(2.1), (I-7)+(2.2), (I-7)+(2.3), (I-7)+(2.4), (I-7)+(2.5), (I-7)+(2.6), (I-7)+(2.7), (I-7)+(2.8), (I-7)+(2.9), (I-7)+(2.10), (I-7)+(2.11), (I-7)+(2.12), (I-7)+(2.13), (I-7)+(2.14), (I-7)+(2.15), (I-7)+(2.16), (I-7)+(2.17), (I-7)+(2.18), (I-7)+(2.19), (I-7)+(2.20), (I-7)+(2.21), (I-7)+(2.22), (1-7)+(2.23), (1-7)+(2.24), (I-7)+(2.25), (I-7)+(2.26), (I-7)+(2.27), (I-7)+(2.28), (I-7)+(2.29), (I-7)+(3.1), (I-7)+(3.2), (I-7)+(3.3), (1-7)+(3.4), (I-7)+(3.5), (I-7)+(3.6), (I-7)+(3.7), (I-7)+(3.8),(I-7)+(3.9),(I-7)+(3.10), (I-7)+(3.11), (I-7)+(3.12), (I-7)+(3.13), (I-7)+(3.14), (I-7)+(3.15), (I-7)+(3.16), (I-7)+(3.17), (I-7)+(3.18), (I-7)+(3.19), (I-7)+(3.20), (I-7)+(3.21), (I-7)+(3.22), (I-7)+(3.23), (I-7)+(3.24), (I-7)+(3.25), (I-7)+(3.26), (I-7)+(3.27), (I-7)+(3.28), (I-7)+(3.29), (I-7)+(3.30), (I-7)+(3.31), (I-7)+(3.32), (I-7)+(3.33), (I-7)+(4.1),(I-7)+(4.2), (I-7)+(4.3), (I-7)+(4.4),(I-7)+(4.5), (I-7)+(4.6), (I-7)+(4.7), (I-7)+(4.8), (I-7)+(4.9), (I-7)+(4.10), (I-7)+(4.11), (I-7)+(4.12), (I-7)+(4.13), (I-7)+(4.14), (I-7)+(5.1), (I-7)+(5.2), (I-7)+(5.3), (I-7)+(5.4), (I-7)+(5.5),(I-7)+(5.6),(I-7)+(5.7),(I-7)+(5.8),(I-7)+(5.9),(I-7)+(5.10), (I-7)+(5.11), (I-7)+(5.12), (I-7)+(5.13), (I-7)+(5.14), (I-7)+(5.15), (I-7)+(5.16), (I-7)+(5.17), (I-7)+(5.18), (I-7)+(5.19), (I-7)+(5.20), (I-7)+(5.21), (I-7)+(5.22), (I-7)+(5.23), (I-7)+(5.24), (I-7)+(5.25), (I-7)+(5.26), (I-7)+(5.27), (I-7)+(5.28), (I-7)+(5.29), (I-7)+(5.30), (I-7)+(5.31), (I-7)+(5.32), (I-7)+(5.33), (I-7)+(5.34), (I-7)+(6.1), (I-7)+(6.2), (I-7)+(6.3), (I-7)+(6.4), (I-7)+(7.1), (I-7)+(7.2), (I-7)+(7.3), (I-7)+(7.4), (I-7)+(7.5), (I-7)+(7.6), (I-7)+(7.7), (I-7)+(7.8), (I-7)+(8.1), (I-7)+(8.2), (I-7)+(8.3), (I-7)+(8.4), (I-7)+(9.1), (I-7)+(9.2), (I-7)+(9.3), (I-7)+(9.4), (I-7)+(9.5), (I-7)+(9.6), (I-7)+(9.7), (I-7)+(9.8), (I-7)+(9.9), (I-7)+(10.1), (I-7)+(10.2), (I-7)+(10.3), (I-7)+(10.4), (I-7)+(10.5), (I-7)+(10.6), (I-7)+(10.7), (I-7)+(10.8), (I-7)+(10.9), (I-7)+(10.10), (I-7)+(10.11), (I-7)+(10.12), (I-7)+(10.13), (I-7)+(10.14), (I-7)+(10.15), (I-7)+(11.1), (I-7)+(11.2), (I-7)+(11.3), (I-7)+(11.4), (I-7)+(11.5), (I-7)+(11.6), (I-7)+(11.7), (I-7)+(12.1), (I-7)+(12.2), (I-7)+(12.3), (I-7)+(12.4), (I-7)+(12.5), (I-7)+(12.6), (I-7)+(12.7), (I-7)+(12.8), (I-7)+(12.9), (I-7)+(12.10), (I-7)+(12.11), (I-7)+(12.12), (I-7)+(12.13), (I-7)+(13.1), (I-7)+(13.2), (I-7)+(13.3), (I-7)+(13.4), (I-7)+(13.5), (I-7)+(13.6), (I-7)+(13.7), (I-7)+(14.1), (I-7)+(14.2), (I-7)+(14.3), (I-7)+(14.4), (I-7)+(14.5), (I-7)+(15.1), (I-7)+(15.2), (I-7)+(15.3), (I-7)+(15.4), (I-7)+(15.5), (I-7)+(15.6), (I-7)+(15.7), (I-7)+(15.8), (I-7)+(15.9), (I-7)+(15.10), (I-7)+(15.11), (I-7)+(15.12), (I-7)+(15.13), (I-7)+(15.14), (I-7)+(15.15), (I-7)+(15.16), (I-7)+(15.17), (I-7)+(15.18), (I-7)+(15.19), (I-7)+(15.20), (I-7)+(15.21), (I-7)+(15.22), (I-7)+(15.23), (I-7)+(15.24), (I-7)+(15.25), (I-7)+(15.26), (I-7)+(15.27), (I-7)+(15.28), (I-7)+(15.29), (I-7)+(15.30), (I-7)+(15.31), (I-7)+(15.32), (I-7)+(15.33), (I-7)+(15.34), (I-7)+(15.35), (I-7)+(15.36), (I-7)+(15.37), (I-7)+(15.38), (I-7)+(15.39), (I-7)+(15.41), (I-7)+(15.42), (I-7)+(15.43), (I-7)+(15.44), (I-7)+(15.45), (I-7)+(15.46), (I-7)+(15.47), (I-7)+(15.48), (I-7)+(15.49), (I-7)+(15.50), (I-7)+(15.51), (I-7)+(15.52), (I-7)+(15.53), (I-7)+(15.54), (I-7)+(15.55), (I-7)+(15.56), (I-7)+(15.57), (I-7)+(15.58), (I-7)+(15.59), (I-7)+(15.60), (I-7)+(15.61), (I-7)+(15.62), (I-7)+(15.63), (I-7)+(15.64), (I-7)+(15.65), (I-7)+(15.66), (I-7)+(15.67), (I-7)+(15.68), (I-7)+(15.69), (I-7)+(15.70), (I-7)+(15.71), (I-7)+(15.72), (I-7)+(15.73), (I-7)+(15.74), (I-7)+(15.75), (I-7)+(15.76), (I-7)+(15.77), (I-7)+(15.78), (I-7)+(15.79), (I-7)+(15.80), (I-7)+(15.81), (I-7)+(15.82), (I-7)+(15.83), (I-7)+(15.84), (I-7)+(15.85), (I-7)+(15.86), (I-7)+(15.87), (I-7)+(15.88), (I-7)+(15.89), (I-7)+(15.90), (I-7)+(15.91), (I-7)+(15.92), (I-7)+(15.93), (I-7)+(15.94).

In a further particularly preferred embodiment this invention is directed to mixtures comprising the compound (I-7) as compound of formula (I) and one component (B), in particular the mixtures (I-7)+(2.1), (I-7)+(2.2), (I-7)+(2.6), (I-7)+(2.8), (I-7)+(2.11), (I-7)+(2.12), (I-7)+(2.13), (I-7)+(2.14), (I-7)+(2.15), (I-7)+(2.16), (I-7)+(2.17), (I-7)+(2.29), (I-7)+(3.1), (I-7)+(3.2), (I-7)+(3.3), (1-7)+(3.4), (I-7)+(3.9), (I-7)+(3.10), (I-7)+(3.12), (I-7)+(3.16), (1-7)+(3.17), (I-7)+(3.22), (I-7)+(4.6), (I-7)+(5.1), (I-7)+(5.4), (I-7)+(5.5), (I-7)+(5.7), (1-7)+(5.8),(I-7)+(5.9),(I-7)+(5.16), (I-7)+(5.23), (I-7)+(5.25), (I-7)+(5.26), (I- 7)+(5.29), (I-7)+(5.30), (I-7)+(7.7), (I-7)+(9.2), (I-7)+(9.4), (I-7)+(9.5), (I-7)+(10.9), (I-7)+(10.10), (I-7)+(12.9), (I-7)+(12.10), (I-7)+(14.4), (I-7)+(15.9), (I-7)+(15.24), (I-7)+(15.25), (I-7)+(15.26), (I-7)+(15.41), (I-7)+(15.42), (1-7)+(15.54), (1-7)+(15.55), (I-7)+(15.56), (I-7)+(15.60), (I-7)+(15.90).

In a preferred embodiment this invention is directed to mixtures comprising the compound (1-8) as compound of formula (I) and one component (B), in particular the mixtures (I-8)+(1.1), (I-8)+(1.2), (I-8)+(1.3), (I-8)+(1.4), (I-8)+(1.5), (I-8)+(1.6), (I-8)+(1.7), (I-8)+(1.8), (I-8)+(1.9), (I-8)+(1.10), (1-8)+(1.11), (I- 8)+(1.12), (I-8)+(1.13), (I-8)+(1.14), (I-8)+(1.15), (I-8)+(1.16), (I-8)+(1.17), (I-8)+(1.18), (I-8)+(1.19), (I-8)+(1.20), (I-8)+(1.21), (I-8)+(1.22), (1-8)+(1.23), (I-8)+(1.24), (I-8)+(1.25), (I-8)+(1.26), (I-8)+(1.27), (I-8)+(1.28), (1-8)+(1.29), (1-8)+(1.30), (I-8)+(1.31), (I-8)+(1.32), (I-8)+(1.33), (I-8)+(1.34), (I-8)+(1.35), (1-8)+(1.36), (I-8)+(1.37), (I-8)+(1.38), (I-8)+(1.39), (I-8)+(1.40), (I-8)+(1.41), (I-8)+(1.42), (I-8)+(1.43), (I-8)+(1.44), (I-8)+(1.45), (I-8)+(1.46), (I-8)+(1.47), (I-8)+(1.48), (I-8)+(1.49), (I-8)+(1.50), (I-8)+(1.51), (I-8)+(1.52), (I-8)+(1.53), (I-8)+(1.54), (I-8)+(1.55), (I-8)+(1.56), (I-8)+(1.57), (I-8)+(1.58), (I-8)+(1.59), (I-8)+(1.60), (I-8)+(1.61), (I-8)+(1.62), (I-8)+(1.63), (I-8)+(1.64), (I-8)+(2.1), (I-8)+(2.2), (1-8)+(2.3), (1-8)+(2.4), (I-8)+(2.5), (I-8)+(2.6), (I-8)+(2.7), (I-8)+(2.8), (I-8)+(2.9), (I-8)+(2.10), (I-8)+(2.11), (I-8)+(2.12), (I-8)+(2.13), (I-8)+(2.14), (I-8)+(2.15), (I-8)+(2.16), (I-8)+(2.17), (I-8)+(2.18), (I-8)+(2.19), (I-8)+(2.20), (I-8)+(2.21), (I-8)+(2.22), (1-8)+(2.23), (I-8)+(2.24), (I-8)+(2.25), (I-8)+(2.26), (I-8)+(2.27), (I-8)+(2.28), (I-8)+(2.29), (I-8)+(3.1), (I-8)+(3.2), (I-8)+(3.3), (1-8)+(3.4), (I-8)+(3.5), (I-8)+(3.6),(I-8)+(3.7),(I-8)+(3.8),(I-8)+(3.9), (1-8)+(3.10), (I-8)+(3.11), (I-8)+(3.12), (I-8)+(3.13), (I- 8)+(3.14), (I-8)+(3.15), (I-8)+(3.16), (I-8)+(3.17), (I-8)+(3.18), (I-8)+(3.19), (I-8)+(3.20), (I-8)+(3.21), (I-8)+(3.22), (I-8)+(3.23), (1-8)+(3.24), (I-8)+(3.25), (I-8)+(3.26), (I-8)+(3.27), (I-8)+(3.28), (I-8)+(3.29), (I-8)+(3.30), (I-8)+(3.31), (1-8)+(3.32), (I-8)+(3.33), (I-8)+(4.1), (I-8)+(4.2), (I-8)+(4.3), (I-8)+(4.4), (I-8)+(4.5), (I-8)+(4.6), (I-8)+(4.7), (I-8)+(4.8), (I-8)+(4.9), (I-8)+(4.10), (I-8)+(4.11), (I-8)+(4.12), (I-8)+(4.13), (I-8)+(4.14), (I-8)+(5.1), (I-8)+(5.2), (I-8)+(5.3), (1-8)+(5.4), (I-8)+(5.5), (I-8)+(5.6),(I-8)+(5.7), (I-8)+(5.8),(I-8)+(5.9), (1-8)+(5.10), (I-8)+(5.11), (I-8)+(5.12), (I- 8)+(5.13), (I-8)+(5.14), (I-8)+(5.15), (5.16), (I-8)+(5.17), (I-8)+(5.18), (I-8)+(5.19), (I-8)+(5.20), (I-8)+(5.21), (I-8)+(5.22), (I-8)+(5.23), (I-8)+(5.24), (I-8)+(5.25), (I-8)+(5.26), (I-8)+(5.27), (I-8)+(5.28), (I-8)+(5.29), (I-8)+(5.30), (I-8)+(5.31), (I-8)+(5.32), (I-8)+(5.33), (I-8)+(5.34), (I-8)+(6.1), (I-8)+(6.2), (I-8)+(6.3), (I-8)+(6.4), (I-8)+(7.1), (I-8)+(7.2), (I-8)+(7.3), (I-8)+(7.4), (I-8)+(7.5), (I-8)+(7.6), (I-8)+(7.7), (I-8)+(7.8), (I-8)+(8.1), (I-8)+(8.2), (I-8)+(8.3), (I-8)+(8.4), (I-8)+(9.1), (I-8)+(9.2), (I-8)+(9.3), (I-8)+(9.4), (I-8)+(9.5), (I-8)+(9.6), (I-8)+(9.7), (I-8)+(9.8), (I-8)+(9.9), (I-8)+(10.1), (I-8)+(10.2), (I-8)+(10.3), (I-8)+(10.4), (I-8)+(10.5), (I-8)+(10.6), (I-8)+(10.7), (I-8)+(10.8), (I-8)+(10.9), (I-8)+(10.10), (I-8)+(10.11), (I-8)+(10.12), (I-8)+(10.13), (I-8)+(10.14), (I-8)+(10.15), (I-8)+(11.1), (I-8)+(11.2), (I-8)+(11.3), (I-8)+(11.4), (I-8)+(11.5), (I-8)+(11.6), (I-8)+(11.7), (I-8)+(12.1), (I-8)+(12.2), (I-8)+(12.3), (I-8)+(12.4), (I-8)+(12.5), (I-8)+(12.6), (I-8)+(12.7), (I-8)+(12.8), (I-8)+(12.9), (I-8)+(12.10), (I-8)+(12.11), (I-8)+(12.12), (I-8)+(12.13), (I-8)+(13.1), (I-8)+(13.2), (I-8)+(13.3), (I-8)+(13.4), (I-8)+(13.5), (I-8)+(13.6), (I-8)+(13.7), (I-8)+(14.1), (I-8)+(14.2), (I-8)+(14.3), (I-8)+(14.4), (I-8)+(14.5), (I-8)+(15.1), (I-8)+(15.2), (I-8)+(15.3), (I-8)+(15.4), (I-8)+(15.5), (I-8)+(15.6), (I-8)+(15.7), (I-8)+(15.8), (I-8)+(15.9), (I-8)+(15.10), (I-8)+(15.11), (I-8)+(15.12), (I-8)+(15.13), (I-8)+(15.14), (I-8)+(15.15), (I-8)+(15.16), (I-8)+(15.17), (I-8)+(15.18), (I-8)+(15.19), (I-8)+(15.20), (I-8)+(15.21), (I-8)+(15.22), (I-8)+(15.23), (I-8)+(15.24), (I-8)+(15.25), (I-8)+(15.26), (I-8)+(15.27), (I-8)+(15.28), (I-8)+(15.29), (I-8)+(15.30), (I-8)+(15.31), (I-8)+(15.32), (I-8)+(15.33), (I-8)+(15.34), (I-8)+(15.35), (I-8)+(15.36), (I-8)+(15.37), (I-8)+(15.38), (I-8)+(15.39), (I-8)+(15.41), (I-8)+(15.42), (I-8)+(15.43), (I-8)+(15.44), (I-8)+(15.45), (I-8)+(15.46), (I-8)+(15.47), (I-8)+(15.48), (I-8)+(15.49), (I-8)+(15.50), (I-8)+(15.51), (I-8)+(15.52), (I-8)+(15.53), (I-8)+(15.54), (I-8)+(15.55), (I-8)+(15.56), (I-8)+(15.57), (I-8)+(15.58), (I-8)+(15.59), (I-8)+(15.60), (I-8)+(15.61), (I-8)+(15.62), (I-8)+(15.63), (I-8)+(15.64), (I-8)+(15.65), (I-8)+(15.66), (I-8)+(15.67), (I-8)+(15.68), (I-8)+(15.69), (I-8)+(15.70), (I-8)+(15.71), (I-8)+(15.72), (I-8)+(15.73), (I-8)+(15.74), (I-8)+(15.75), (I-8)+(15.76), (I-8)+(15.77), (I-8)+(15.78), (I-8)+(15.79), (I-8)+(15.80), (I-8)+(15.81), (I-8)+(15.82), (I-8)+(15.83), (I-8)+(15.84), (I-8)+(15.85), (I-8)+(15.86), (I-8)+(15.87), (I-8)+(15.88), (I-8)+(15.89), (I-8)+(15.90), (I-8)+(15.91), (I-8)+(15.92), (I-8)+(15.93), (I-8)+(15.94).

In a further particularly preferred embodiment this invention is directed to mixtures comprising the compound (I-8) as compound of formula (I) and one component (B), in particular the mixtures (I-8)+(2.1), (I-8)+(2.2), (I-8)+(2.6), (I-8)+(2.8), (I-8)+(2.11), (I-8)+(2.12), (I-8)+(2.13), (I-8)+(2.14), (I-8)+(2.15), (I-8)+(2.16), (I-8)+(2.17), (I-8)+(2.29), (I-8)+(3.1), (I-8)+(3.2), (I-8)+(3.3), (I-8)+(3.4),(I-8)+(3.9), (I-8)+(3.10), (I-8)+(3.12), (I-8)+(3.16), (I-8)+(3.17), (I-8)+(3.22), (I-8)+(4.6), (I-8)+(5.1), (I-8)+(5.4), (I-8)+(5.5),(I-8)+(5.7),(I-8)+(5.8),(I-8)+(5.9),(I-8)+(5.16), (I-8)+(5.23), (I-8)+(5.25), (I-8)+(5.26), (I-8)+(5.29), (I-8)+(5.30), (I-8)+(7.7), (I-8)+(9.2), (I-8)+(9.4), (I-8)+(9.5), (I-8)+(10.9), (I-8)+(10.10), (I-8)+(12.9), (I-8)+(12.10), (I-8)+(14.4), (I-8)+(15.9), (I-8)+(15.24), (I-8)+(15.25), (I-8)+(15.26), (I-8)+(15.41), (I-8)+(15.42), (I-8)+(15.54), (I-8)+(15.55), (I-8)+(15.56), (I-8)+(15.60), (I-8)+(15.90).

If the active compounds in the active compound combinations according to the invention are present in certain weight ratios, the synergistic effect is particularly pronounced. However, the weight ratios of the active compounds in the active compound combinations can be varied within a relatively wide range.

In the combinations according to the invention the compounds (A) and (B) are present in a synergistically effective weight ratio of A:B in a range of 500:1 to 1:5000, preferably in a weight ratio of 300:1 to 1:2000, most preferably in a weight ratio of 200:1 to 1:1000. Further ratios of A:B which can be used according to the present invention with increasing preference in the order given are: 250:1 to 1:250, 220:1 to 1:220, 200:1 to 1:200, 170:1 to 1:170, 140:1 to 1:140, 120:1 to 1:120, 100:1 to 1:100, 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Further preferred ratios of A:B which can be used according to the present invention are: 1:1 to 1:5000, 1:1 to 1:2000, 1:1 to 1:1000, 1:10 to 1:5000, 1:10 to 1:2000, 1:10 to 1:1000, 1:20 to 1:5000, 1:20 to 1:2000, 1:20 to 1:1000, 1:100 to 1:5000, 1:100 to 1:2000, 1:100 to 1:1000, 1:200 to 1:5000, 1:200 to 1:2000, 1:200 to 1:1000, 1:500 to 1:5000, 1:500 to 1:2000, 1:500 to 1:1000.

Further preferred ratios of A:B which can be used according to the present invention are: 500:1 to 1:50, 500:1 to 1:2, 500:1 to 10:1, 500:1 to 20:1, 500:1 to 100:1, 300:1 to 1:50, 300:1 to 1:2, 300:1 to 10:1, 300:1 to 20:1, 300:1 to 100:1, 250:1 to 1:50, 250:1 to 1:2, 250:1 to 10:1, 250:1 to 20:1, 250:1 to 100:1, 200:1 to 1:50, 200:1 to 1:2, 200:1 to 10:1, 200:1 to 20:1, 200:1 to 100:1.

Where a compound (A) or a compound (B) can be present as mixtures of various possible isomeric forms, in particular of stereoisomers, such as, for example, E and Z, threo and erythro, and also optical isomers, and, if appropriate, also of tautomers. What is claimed are both the E and the Z isomers and the threo and erythro and also the optical isomers (R and S), any mixtures of these isomers, and also the possible tautomeric forms.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, Ci-C4alkane- or aryl-sulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or the compounds (B) in free form and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts.

According to the invention the expression "combination" stands for the various combinations of compounds (A) and (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A) and (B) is not essential for working the present invention.

Composition/Formulation

The present invention furthermore relates to compositions for combating/controlling undesirable microorganisms comprising the active compound combinations according to the invention. Preferably, the compositions are fungicidal compositions comprising agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, SolvessoTM, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

Furthermore the invention relates to a method of combating undesirable microorganisms, characterized in that the active compound combinations according to the invention are applied to the phytopathogenic fungi and/or their habitat.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 per cent by weight of the composition according to the invention.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures therof.

Examples of thickeners are polysaccharides, e.g. xanthan gum or veegum, silicates, e.g. attapulgite, bentonite as well as fine-particle silica.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The inventive compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

In general, the compositions according to the invention comprise between 0.05 and 99 per cent by weight, 0.01 and 98 per cent by weight, preferable between 0.1 and 95 per cent by weight, particularly preferred between 0.5 and 90 per cent by weight of the active compound combination according to the invention, very particularly preferable between 10 and 70 per cent by weight.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive composition may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The compositions according to the invention do not only comprise ready-to-use compositions which can be applied with suitable apparatus to the plant or the seed, but also commercial concentrates which have to be diluted with water prior to use.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;* diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondite, P. triticina, P. graminis* or *P. striiformis; Uromyces* species, for example *Uromyces appendiculatus;* diseases caused by pathogens from the group of the Oomycetes, for example *Albugo* species, for example *Algubo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidia form: Drechslera, Syn: Helminthosporium), *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans, Leptosphaeria nodorum; Magnaporthe* species, for example *Magnaporthe grisea; Microdochium* species, for example *Microdochium nivale; Mycosphaerella* species, for example *Mycosphaerella graminicola, M. arachidicola* and *M. fijiensis; Phaeosphaeria* species, for example *Phaeosphaeria nodorum; Pyrenophora* species, for example *Pyrenophora teres, Pyrenophora tritici repentis; Ramularia* species, for example *Ramularia collo-cygni, Ramularia areola; Rhynchosporium* species, for example *Rhynchosporium secalis; Septoria* species, for example *Septoria apii, Septoria lycopersii; Typhula* species, for example *Typhula incarnata; Venturia* species, for example *Venturia inaequalis;* root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola;* ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum;* diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici;* fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticilium* species, for example *Verticilium alboatrum;* seed and soilborne decay, mould, wilt, rot and damping-off diseases caused, for example, by *Altermaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaform: Drechslera, Bipolaris Syn: Helminthosporium); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii;* Septoria species, caused for example by *Septoria nodorum; Typhula* species, caused for example by *Typhula incarnata; Verticillium* species, caused for example by *Verticillium dahliae;* cancers, galls and witches' broom caused, for example, by *Nectria* species, for example *Nectria galligena;* wilt diseases caused, for example, by *Monilinia* species, for example *Monilinia laxa;* leaf blister or leaf curl diseases caused, for example, by *Exobasidium* species, for example *Exobasidium vexans*;

*Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; Eutypa dyeback, caused for example by *Eutypa lata*; Ganoderma diseases caused for example by *Ganoderma boninense*; Rigidoporus diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani; Helminthosporium* species, for example *Helminthosporium solani*;

Club root caused, for example, by *Plasmodiophora* species, for example *Plamodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachryrnans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncaturn*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycine*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidematum, Pythium irregulare, Pythium debalyanum, Pythium myriotylum, Pythium ultanum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active compositions, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

In particular, the mixtures and compositions according to the invention are suitable for controlling the following plant diseases:

*Albugo* spp. (white rust) on ornamental plants, vegetable crops (e.g. *A. candida*) and sunflowers (e.g. *A. tragopogonis*); *Alternaria* spp. (black spot disease, black blotch) on vegetables, oilseed rape (e.g. *A. brassicola* or *A. brassicae*), sugar beet (e.g. *A. tenuis*), fruit, rice, soybeans and also on potatoes (e.g. *A. solani* or *A. alternate*) and tomatoes (e.g. *A. solani* or *A. alternate*) and *Alternaria* spp. (black head) on wheat; *Aphanomyces* spp. on sugar beet and vegetables; *Ascochyta* spp. on cereals and vegetables, e.g. *A. tritici* (Ascochyta leaf blight) on wheat and *A. hordei* on barley; *Bipolaris* and *Drechslera* spp. (teleomorph: *Cochliobolus* spp.), e.g. leaf spot diseases (*D. maydis* and *B. zeicola*) on corn, e.g. glume blotch (*B. sorokiniana*) on cereals and e.g. *B. oryzae* on rice and on lawn; *Blumeria* (old name: *Erysiphe*) *graminis* (powdery mildew) on cereals (e.g. wheat or barley); *Botryosphaeria* spp. ('Slack Dead Arm Disease') on grapevines (e.g. *B. obtuse*); *Botrytis cinerea* (teleomorph: *Botryotinia fuckeliana*: gray mold, gray rot) on soft fruit and pomaceous fruit (inter alia strawberries), vegetables (inter alia lettuce, carrots, celeriac and cabbage), oilseed rape, flowers, grapevines, forest crops and wheat (ear mold); *Bremia lactucae* (downy mildew) on lettuce; *Ceratocystis* (syn. *Ophiostoma*) spp. (blue stain fungus) on deciduous trees and coniferous trees, e.g. *C. ulmi* (Dutch elm disease) on elms; *Cercospora* spp. (Cereospora leat spot) on corn (e.g. *C. zeae-maydis*), rice, sugar beet (e.g. *C. beticola*), sugar cane, vegetables, coffee, soybeans (e.g. *C. sojina* or *C. kikuchii*) and rice; *Cladosporium* spp. on tomato (e.g. *C. fulvum*: tomato leaf mold) and cereals, e.g. *C. herbarum* (ear rot) on wheat; *Claviceps purpurea* (ergot) on cereals; *Cochliobolus* (anamorph: *Helminthosporium* or *Bipolaris*) spp. (leaf spot) on corn (e.g. *C. carbonum*), cereals (e.g. *C. sativus*, anamorph: *B. sorokiniana*: glume blotch) and rice (tor example *C. miyabeanus*, anamorph: *H. oryzae*); *Colletotrichum* (teleomorph: *Glomerella*) spp. (anthracnosis) on cotton (e.g. *C. gossypii*), corn (e.g. *C. graminicola*: stem rot and anthracnosis), soft fruit, potatoes (e.g. *C. coccodes*: wilt disease), beans (e.g. *C. lindemuthianum*) and soybeans (e.g. *C. truncatum*); *Corticium* spp., e.g. *C. sasakii* (sheath blight) on rice; *Corynespora cassiicola* (leaf spot) on soybeans and ornamental plants; *Cycloconium* spp., e.g. *C. oleaginum* on olives; *Cylindrocarpon* spp. (e.g. fruit tree cancer or black foot disease of grapevine, teleomorph: *Nectria* or *Neonectria* spp.) on fruit trees, grapevines (e.g. *C. liriodendn*; teleomorph: *Neonectria liriodendra*, black foot disease) and many ornamental trees; *Dematophora* (teleomorph: *Rosellinia*) *necatrix* (root/stem rot) on soybeans; *Diaporthe* spp. e.g. *D. phaseolorum* (stem disease) on soybeans; *Drechslera* (syn. *Helminthosporium*, teleomorph: *Pyrenophora*) spp. on corn, cereals, such as barley (e.g. *D. teres*, net blotch) and on wheat (e.g. *D. tritici-repentis*: DTR leaf spot), rice and lawn; Esca disease (dieback of grapevine, apoplexia) on grapevines, caused by *Fonnitiporia* (syn. *Phellinus*) *punctata, F mediterranea. Phaeomoniella chlamydospora* (old name *Phaeoacremonium chlamydosporum*), *Phaeoacremonium aleophilum* and/or *Botryosphaeria obtusa; Elsinoe* spp. on pome fruit (*E. pyri*) and soft fruit (*E. veneta*: anthracnosis) and also grapevines (*E. ampelina*: anthracnosis); *Entyloma oryzae* (leaf smut) on rice; *Epicoccum* spp. (black head) on wheat; *Erysiphe* spp. (powdery mildew) on sugar beet (*E. betae*), vegetables (e.g. *E. pisi*), such as cucumber species (e.g. *E. cichoracearum*) and cabbage species, such as oilseed rape (e.g. *E. cruciferarum*); *Eutypa fata* (Eutypa cancer or dieback, anamorph: *Cytospo-*

*rina lata*, syn. *Libertella blepharis*) on fruit trees, grapevines and many ornamental trees; *Exserohilum* (syn. *Helminthosporium*) spp. on corn (e.g. *E. turcicum*); *Fusarium* (teleomorph: *Gibberella*) spp. (wilt disease, root and stem rot) on various plants, such as e.g. *F. graminearum* or *F. culmorum* (root rot and silver-top) on cereals (e.g. wheat or barley), *F. oxysporum* on tomatoes, *F. solani* on soybeans and *F. verticillioides* on corn; *Gaeumannomyces graminis* (takeall) on cereals (e.g. wheat or barley) and corn; *Gibberella* spp. on cereals (e.g. *G. zeae*) and rice (e.g. *G. fujikuroi*: bakanae disease); *Glomerella cingulata* on grapevines, pomaceous fruit and other plants and *G. gossypii* on cotton; grainstaining complex on rice; *Guignardia bidwellii* (black rot) on grapevines; *Gymnosporangium* spp. on Rosaceae and juniper, e.g. *G. sabinae* (pear rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on grapevines; *Macrophomina phaseolina* (syn. *phaseoli*) (root/stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa. M. fructicola* and *M. fructigena* (blossom and twig blight) on stone fruit and other Rosaceae; *Mycosphaerella* spp. on cereals, bananas, soft fruit and peanuts, such as e.g. *M. graminicola* (anamorph: *Septoria tritici*, Septoria leaf blotch) on wheat or *M. fijiensis* (Sigatoka disease) on bananas; *Peronospora* spp. (downy mildew) on cabbage (e.g. *P. brassicae*), oilseed rape (e.g. *P. parasitica*), bulbous plants (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on grapevines (e.g. *P. tracheiphila* and *P. tetraspora*) and soybeans (e.g. *P. gregata*: stem disease); *Phoma lingam* (root and stem rot) on oilseed rape and cabbage and *P. betae* (leaf spot) on sugar beet; *Phomopsis* spp. on sunflowers, grapevines (e.g. *P. viticola*: dead-arm disease) and soybeans (e.g. stem canker/stem blight: *P. phaseoli*, teleomorph: *Diaporthe phaseolorum*); *Physoderma maydis* (brown spot) on corn; *Phytophthora* spp. (wilt disease, root, leaf, stem and fruit rot) on various plants, such as on bell peppers and cucumber species (e.g. *P. capsici*), soybeans (e.g. *P. megaspenna*, syn. *P. sojae*), potatoes and tomatoes (e.g. *P. infestans*. late blight and brown rot) and deciduous trees (e.g. *P. ramorum* sudden oak death); *Plasmodiophora brassicae* (club-root) on cabbage, oilseed rape, radish and other plants; *Plasmopara* spp., e.g. *P. viticola* (peronospora of grapevines, downy mildew) on grapevines and *P. halstedii* on sunflowers; *Podosphaera* spp. (powdery mildew) on Rosaceae, hops, pomaceaus fruit and soft fruit, e.g. *P. leucotricha* on apple; *Polymyxa* spp., e.g. on cereals, such as barley and wheat (*P. graminis*) and sugar beet (*P. betae*) and the viral diseases transmitted thereby; *Pseudocerco-sporella herpotrichoides* (eyespot/stem break, teleomorph: *Tapesia yallundae*) on cereals. e.g. wheat or barley; *Pseudoperonospora* (downy mildew) on various plants, e.g. *P. cubensis* on cucumber species or *P. humili* on hops; *Pseudopezicula tracheiphila* (angular leaf scorch, anamorph *Phialophora*) on grapevines; *Puccinia* spp. (rust disease) on various plants, e.g. *P. triticina* (brown rust of wheat), *P. striifonnis* (yellow rust). *P. hordei* (dwarf leaf rust), *P. graminis* (black rust) or *P. recondita* (brown rust of rye) on cereals, such as e.g. wheat, barley or rye. P. kuehnii on sugar cane and, e.g., on asparagus (e.g. *P. asparagi*); *Pyrenophora* (anamorph: *Drechslera*) *tritici-repentis* (speckled leaf blotch) on wheat or *P. teres* (net blotch) on barley; *Pyricularia* spp., e.g. *P. oryzae* (teleomorph:

*Magnaporthe grisea*. rice blast) on rice and *P. grisea* on lawn and cereals; *Pythium* spp. (damping-off disease) on lawn, rice, corn, wheat, cotton, oilseed rape, sunflowers, sugar beet, vegetables and other plants (e.g. *P. ultimum* or *P. aphanidennatum*); *Ramularia* spp., e.g. *R. collo-cygni* (*Ramularia* leaf and lawn spot/physiological leaf spot) on barley and *R. beticola* on sugar beet; *Rhizoctonia* spp. on cotton, rice, potatoes, lawn, corn, oilseed rape, potatoes, sugar beet, vegetables and on various other plants, for example *R. solani* (root and stern rot) on soybeans, *R. solani* (sheath blight) on rice or *R. cerealis* (sharp eyespot) on wheat or barley; *Rhizopus stolonifer* (soft rot) on strawberries, carrots, cabbage, grapevines and tomato; *Rhynchosporium secalis* (leaf spot) on barley, rye and triticale; *Sarocladium oryzae* and *S. attenuatum* (sheath rot) on rice; *Sclerotinia* spp. (stem or white rot) on vegetable and field crops, such as oilseed rape, sunflowers (e.g. *Sclerotinia sclerotiorum*) and soybeans (e.g. *S. rolfsii*), *Septoria* spp. on various plants, e.g. *S. glycines* (leaf spot) on soybeans, *S. tritici* (Septoria leaf blotch) on wheat and *S.* (syn. *Stagonospora*) *nodorum* (leaf blotch and glume blotch) on cereals; *Uncinula* (syn. *Erysiphe*) *necator* (powdery mildew, anamorph: *Oidium tuckeri*) on grapevines; *Setospaeria* spp. (leaf spot) on corn (e.g. *S. turcicum*, syn. *Helminthosporium turcicum*) and lawn; *Sphacelotheca* spp. (head smut) on corn, (e.g. *S. reiliana*: kernel smut), millet and sugar cane; *Sphaerotheca fuliginea* (powdery mildew) on cucumber species; *Spongospora subterranea* (powdery scab) on potatoes and the viral diseases transmitted thereby; *Stagonospora* spp. on cereals, e.g. *S. nodorum* (leaf blotch and glume blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (curly-leaf disease) on peach and *T. pruni* (plum-pocket disease) on pi ums; *Thielaviopsis* spp. (black root rot) on tobacco, pome fruit, vegetable crops, soybeans and cotton, e.g. *T. basicola* (syn. *Chalara elegans*); *Tilletia* spp. (bunt or stinking smut) on cereals, such as e.g. *T. tritici* (syn. *T. caries*, wheat bunt) and *T. controversa* (dwarf bunt) on wheat; *Typhula incarnata* (gray snow mold) on barley or wheat; *Urocystis* spp., e.g. *U. occulta* (flag smut) on rye; *Uromyces* spp. (rust) on vegetable plants, such as beans (e.g. *U. appendiculatus*, syn. *U. phaseoll*) and sugar beet (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears and *Verticillium* spp. (leaf and shoot wilt) on various plants, such as fruit trees and ornamental trees, grapevines, soft fruit, vegetable and field crops, such as e.g. *V. dahliae* on strawberries, oilseed rape, potatoes and tomatoes.

Plant Growth Regulation

In some cases, the inventive compositions can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The inventive active combinations intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active combinations according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active combinations according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health / plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectolitre weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting up-take and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology*, 2007, 11, 319-341; *Applied Soil Ecology*, 2000, 15, 169-182.)

The improvement in greening / improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photo-chemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further comprises a method for treating seed.

The invention further relates to seed which has been treated by one of the methods described in the previous paragraph. The inventive seeds are employed in methods for the protection of seed from unwanted micro-organisms. In these methods, seed treated with at least one inventive active ingredient is used.

The inventive compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European maize borer and/or the Western maize rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272, 417, 4,245,432, 4,808,430, 5,876,739, US 2003/0176428 Al, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are non-ionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophens and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive compositions can also be used in the protection of materials, for protection of industrial materials against attack and destruction by unwanted microorganisms, for example fungi and insects.

In addition, the inventive combinations can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active combinations may prevent adverse effects, such as rotting, decay, discoloration, decoloration or formation of mould.

In the case of treatment of wood the compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive combinations can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Alternaria*, such as *Alternaria tenuis; Aspergillus*, such as *Aspergillus niger;*

*Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive combinations also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive combinations can therefore be used both in medical and in non-medical applications.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi-technology or microRNA—miRNA-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the combinations are resistant against one or more biotic stresses, i.e. said plants show a better defense against animal and microbial pests, such as against nematodes, insects, mites, phytopathogenic fungi, bacteria, viruses and/or viroids.

Examples of nematode or insect resistant plants are described in e.g. U.S. patent applications Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in Brassica species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Science 1983, 221, 370-371), the CP4 gene of the bacterium *Agrobacterium* sp. (Curr. Topics Plant Physiol. 1992, 7, 139-145), the genes encoding a Petunia EPSPS (Science 1986, 233, 478-481), a Tomato EPSPS (J. Biol. Chem. 1988, 263, 4280-4289), or an Eleusine EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/036782, WO 03/092360, WO 2005/012515 and WO 2007/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent applications Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943801 or 12/362,774. Plants comprising other genes that confer glyphosate tolerance, such as decarboxylase genes, are described in e.g. U.S. patent applications Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from Streptomyces species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (*Weed Science* 2002, 50, 700-712), but also, in U.S. Pat. Nos. 5,605,011; 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782 and U.S. patent application Ser. No. 61/288958.

Other plants tolerant to imidazolinone and/or sulfonylurea can be obtained by induced mutagenesis, selection in cell cultures in the presence of the herbicide or mutation breeding as described for example for soy-beans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes CrylAb, CrylAc, CrylB, CrylC, CrylD, CrylF, Cry2Ab, Cry3Aa, or Cry3Bb or insecticidal portions thereof (e.g. EP-A 1 999 141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (*Nat. Biotechnol.* 2001, 19, 668-72; *Applied Environm. Microbiol.* 2006, 71, 1765-1774) or the binary toxin made up of the CrylA or CrylF proteins and the Cry2Aa or Cry2Ab or Cry2Ae proteins (U.S. patent application Ser. No. 12/214,022 and EP-A 2 300 618); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1 A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Applications 61/126083 and 61/195019), or the binary toxin made up of the VIP3 protein and the Cry2Aa or Cry2Ab or Cry2Ae proteins (U.S. patent application Ser. No. 12/214, 022 and EP-A 2 300 618).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO 2006/045633, EP-A 1 807 519, or EP-A 2 018 431.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP-A 1 794 306, WO 2006/133827, WO 2007/107326, EP-A 1 999 263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP-A 0 571 427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, WO 2008/017518, WO 2008/080630, WO 2008/080631, EP 07090007.1, WO 2008/090008, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, US 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936, WO 2010/012796, WO 2010/003701, 2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP-A 0 663 956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP-A 0 728 213, 3) transgenic plants which produce hyaluronan, as for example disclosed in WO 2006/032538, WO 2007/039314, WO 2007/039315, WO 2007/039316, JP-A 2006-304779, and WO 2005/012529.

4) transgenic plants or hybrid plants, such as onions with characteristics such as 'high soluble solids content', low pungency' (LP) and/or 'long storage' (LS), as described in U.S. patent applications Ser. Nos. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549.

b) Plants, such as cotton plants, containing an altered form of rsw2 or rsw3 homologous nucleic acids as described in WO 2004/053219.

c) Plants, such as cotton plants, with increased expression of sucrose phosphate synthase as described in WO 01/17333.

d) Plants, such as cotton plants, with increased expression of sucrose synthase as described in WO 02/45485.

e) Plants, such as cotton plants, wherein the timing of the plasmodesmatal gating at the basis of the fiber cell is altered, e.g. through downregulation of fiber-selective β-1,3-glucanase as described in WO 2005/017157, or as described in WO 2009/143995.

f) Plants, such as cotton plants, having fibers with altered reactivity, e.g. through the expression of N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related Brassica plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190, or 5,965,755 c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control - herbicide tolerance, deposited as PTA-6233, described in WO 2005/103266 or US-A 2005-216969); Event 3006-210-23 (cotton, insect control—herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control - herbicide tolerance, deposited as ATCC PTA-11508, described in WO 2011/075593); Event 43A47 (corn, insect control - herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control—herbicide tolerance, deposited as ATCC PTA 11384, described in US-A 2006-070139); Event DAS-59132 (corn, insect control - herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinj al, insect control, not deposited, described in WO 2007/091277); Event FI117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control - herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in US 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-0138504); Event MON87701 (soybean, insect control, deposited as ATCC PTA-8194, described in US-A 2009-130071 or WO 2009/064652); Event MON87705 (soybean, quality trait - herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control - herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control - herbicide tolerance, deposited as ATCC PTA-850 or PTA-2485, described in WO 01/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control—herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control—herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control - herbicide tolerance, not deposited, described in US-A 2005-039226 or WO 2004/099447); Event VIP1034 (corn, insect control —herbicide tolerance, deposited as ATCC PTA-3925., described in WO 03/052073), Event 32316 (corn, insect control-herbicide tolerance,deposited as PTA-11507, described in WO 2011/084632), Event 4114 (com,insect control-herbicide tolerance,deposited as PTA-11506, described in WO 2011/084621).

Application Rates and Timing

When using the inventive combinations as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive compositions can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The method of treatment according to the invention also provides the use or application of compounds (A) and (B) and/or (C) in a simultaneous, separate or sequential manner If the single active ingredients are applied in a sequential manner, i.e. at different times, they are applied one after the other within a reasonably short period, such as a few hours or days. Preferably the order of applying the compounds (A) and (B) and/or (C) is not essential for working the present invention.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The advanced fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S.

R., "Calculating Synergistic and Antagonistic Responses of Herbicide Combinations", Weeds 1967, 15, 20-22):

If
X is the efficacy when active compound A is applied at an application rate of m ppm (or g/ha),
Y is the efficacy when active compound B is applied at an application rate of n ppm (or g/ha),
E is the efficacy when the active compounds A and B are applied at application rates of m and n ppm (or g/ha), respectively, and
then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the following examples. However the invention is not limited to the examples.

EXAMPLE 1

Alternaria test (tomatoes)/preventive
Solvent: 24.5 parts by weight of acetone
24.5 parts by weight of dimethylacetamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Alternaria solani*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed.

the untreated control, while an efficacy of 100% means that no disease is observed.

The table below clearly shows that the observed activity of the active compound combination according to the invention is greater than the calculated activity, i.e. a synergistic effect is present.

TABLE 1

*Alternaria* test (tomatoes)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 25 | 20 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 25 | 0 | |
| 2.6 | fluopyram | 1 | 48 | |
| 2.21 | penthiopyrad | 0.5 | 39 | |
| (I-1) + 2.6 | 25:1 | 25 + 1 | 70 | 58 |
| (I-3) + 2.6 | 25:1 | 25 + 1 | 53 | 48 |
| (I-1) + 2.21 | 50:1 | 25 + 0.5 | 78 | 51 |
| (I-3) + 2.21 | 50:1 | 25 + 0.5 | 60 | 39 |

*found = activity found
**calc. = activity calculated using Colby's formula

TABLE 2

*Alternaria* test (tomatoes)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 100 | 34 | |

TABLE 2-continued

*Alternaria* test (tomatoes)/preventive

| | Active compounds | Application rate of active compound in ppm a.i. | Efficacy in % found* | calc.** |
|---|---|---|---|---|
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 100 | 36 | |
| | | 25 | 30 | |
| 15.60 | 2,6-dimethyl-1H,5H-[1,4]dithiino[2,3-c:5,6-c']di-pyrrole-1,3,5,7(2H,6H)-tetrone | 50 | 32 | |
| 5.4 | chlorothalonil | 20 | 5 | |
| 5.16 | folpet | 10 | 0 | |
| 5.29 | propineb | 5 | 0 | |
| 7.7 | pyrimethanil | 20 | 32 | |
| (I-1) + 15.60 | 2:1 | 100 + 50 | 65 | 55 |
| (I-1) + 5.4 | 5:1 | 100 + 20 | 61 | 37 |
| (I-3) + 5.4 | 5:1 | 100 + 20 | 71 | 39 |
| (I-1) + 5.16 | 10:1 | 100 + 10 | 41 | 34 |
| (I-3) + 5.16 | 10:1 | 100 + 10 | 64 | 36 |
| (I-3) + 5.29 | 5:1 | 25 + 5 | 45 | 30 |
| (I-3) + 7.7 | 5:1 | 100 + 20 | 63 | 56 |

*found = activity found
**calc. = activity calculated using Colby's formula

EXAMPLE 2

Phytophthora test (tomatoes)/preventive
Solvent: 24.5 parts by weight of acetone
24.5 parts by weight of dimethylacetamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Phytophthora infestans*. The plants are then placed in an incubation cabinet at approximately 20° C. and a relative atmospheric humidity of 100%.

The test is evaluated 3 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE 3

*Phytophthora* test (tomatoes)/protective

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 0.005 | 82 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 0.0025 | 65 | |
| 3.1 | ametoctradin | 2.5 | 22 | |
| | | 1.25 | 15 | |
| 15.9 | cymoxanil | 5 | 0 | |
| | | 2.5 | 0 | |
| 14.4 | fluazinam | 2.5 | 0 | |
| 15.24 | fosetyl-Al | 5 | 0 | |
| | | 2.5 | 0 | |
| 12.10 | mefenoxam | 2.5 | 36 | |
| | | 1.25 | 10 | |
| 15.41 | phosphorous acid | 5 | 13 | |
| | | 2.5 | 0 | |
| (I-1) + 3.1 | 1:500 | 0.005 + 2.5 | 99 | 86 |
| (I-3) + 3.1 | 1:500 | 0.0025 + 1.25 | 94 | 70 |
| (I-1) + 15.9 | 1:1000 | 0.005 + 5 | 89 | 82 |
| (I-3) + 15.9 | 1:1000 | 0.0025 + 2.5 | 80 | 65 |
| (I-3) + 14.4 | 1:1000 | 0.0025 + 2.5 | 84 | 65 |
| (I-1) + 15.24 | 1:1000 | 0.005 + 5 | 93 | 82 |

TABLE 3-continued

Phytophthora test (tomatoes)/protective

| Active compounds | | Application rate of active compound in ppm a.i. | Efficacy in % found* | calc.** |
|---|---|---|---|---|
| (I-3) + 15.24 | 1:1000 | 0.0025 + 2.5 | 93 | 65 |
| (I-1) + 12.10 | 1:500 | 0.005 + 2.5 | 98 | 88 |
| (I-3) + 12.10 | 1:500 | 0.0025 + 1.25 | 83 | 69 |
| (I-1) + 15.41 | 1:1000 | 0.005 + 5 | 94 | 84 |
| (I-3) + 15.41 | 1:1000 | 0.0025 + 2.5 | 74 | 65 |

*found = activity found
**calc. = activity calculated using Colby's formula

TABLE 4

Phytophthora test (tomatoes)/protective

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 0.01<br>0.005 | 77<br>67 | |
| (I-3) | 2-{3-[2-(1-{[3,5-bis-(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 0.01<br>0.005 | 28<br>5 | |
| 3.2 | amisulbrom | 1 | 19 | |
| 9.1 | benthiavalicarb | 0.5 | 52 | |
| 3.4 | cyazofamid | 0.2 | 8 | |
| 9.2 | dimethomorph | 1 | 20 | |
| 3.10 | fenamidone | 0.5 | 3 | |
| 9.4 | iprovalicarb | 2 | 9 | |
| 15.90 | pentyl{6-[({[(1-methyl-1H-tetrazol-5-yl)(phenyl)methylidene]amino}oxy)methyl]pyridin-2-yl}carbamate | 0.2 | 10 | |
| (I-1) + 3.2 | 1:100 | 0.01 + 1 | 97 | 87 |
| (I-1) + 9.1 | 1:100 | 0.005 + 0.5 | 91 | 84 |
| (I-3) + 9.1 | 1:100 | 0.005 + 0.5 | 81 | 54 |
| (I-3) + 3.4 | 1:40 | 0.005 + 0.2 | 62 | 13 |
| (I-3) + 9.2 | 1:100 | 0.01 + 1 | 64 | 42 |
| (I-3) + 3.10 | 1:100 | 0.005 + 0.5 | 94 | 8 |
| (I-3) + 9.4 | 1:200 | 0.01 + 2 | 83 | 34 |
| (I-1) + 15.90 | 1:40 | 0.005 + 0.2 | 83 | 70 |
| (I-3) + 15.90 | 1:40 | 0.005 + 0.2 | 50 | 15 |

*found = activity found
**calc. = activity calculated using Colby's formula

TABLE 5

Phytophthora test (tomatoes)/protective

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 0.0025 | 52 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 0.01<br>0.0025 | 87<br>59 | |
| 2.29 | benzovindiflupyr | 2.5 | 0 | |
| 2.27 | N-[1-(2,4-dichlorophenyl)-1-methoxypropan-2-yl}-3-(difluoromethyl)-1-methyl-1H-pyrazole-4-carboxamide | 10<br>2.5 | 8<br>0 | |

TABLE 5-continued

Phytophthora test (tomatoes)/protective

| Active compounds | | Application rate of active compound in ppm a.i. | Efficacy in % found* | calc.** |
|---|---|---|---|---|
| 2.8 | fluxapyroxad | 2.5 | 0 | |
| 2.12 | isopyrazam | 2.5 | 0 | |
| 2.21 | penthiopyrad | 2.5 | 0 | |
| (I-1) + 2.29 | 1:1000 | 0.0025 + 2.5 | 60 | 52 |
| (I-1) + 2.27 | 1:1000 | 0.0025 + 2.5 | 67 | 52 |
| (I-3) + 2.27 | 1:1000 | 0.01 + 10 | 93 | 88 |
| (I-3) + 2.8 | 1:1000 | 0.0025 + 2.5 | 77 | 59 |
| (I-1) + 2.12 | 1:1000 | 0.0025 + 2.5 | 62 | 52 |
| (I-1) + 2.21 | 1:1000 | 0.0025 + 2.5 | 63 | 52 |

* found = activity found
** calc. = activity calculated using Colby's formula

TABLE 6

Phytophthora test (tomatoes)/protective

| Active compounds | | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 0.0025 | 48 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 0.0025 | 79 | |
| 5.5 | copper hydroxide | 2.5 | 18 | |
| 5.8 | copper oxychloride | 2.5 | 0 | |
| 5.25 | metiram | 2.5 | 15 | |
| 10.10 | propamocarb—HCl | 2.5 | 0 | |
| (I-1) + 5.5 | 1:1000 | 0.0025 + 2.5 | 92 | 57 |
| (I-3) + 5.5 | 1:1000 | 0.0025 + 2.5 | 93 | 83 |
| (I-1) + 5.8 | 1:1000 | 0.0025 + 2.5 | 75 | 48 |
| (I-1) + 5.25 | 1:1000 | 0.0025 + 2.5 | 93 | 56 |
| (I-1) + 10.10 | 1:1000 | 0.0025 + 2.5 | 67 | 48 |

*found = activity found
**calc. = activity calculated using Colby's formula

EXAMPLE 3

Sphaerotheca test (cucumbers)/preventive
Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of Sphaerotheca fuliginea. The plants are then placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE 7

Sphaerotheca test (cucumbers)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 100 | 19 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 100 | 43 | |
| 2.29 | benzovindiflupyr | 0.5 | 0 | |
| 2.1 | bixafen | 1 | 10 | |
| 2.27 | N-[1-(2,4-dichlorophenyl)-1-methoxypropan-2-yl]-3-(difluoromethyl)-1-methyl-1H-pyrazole-4-carboxamide | 4 | 81 | |
| 2.6 | fluopyram | 4 | 19 | |
| 2.8 | fluxapyroxad | 1 | 38 | |
| 2.12 | isopyrazam | 1 | 19 | |
| 2.12 | penthiopyrad | 2 | 57 | |
| (I-1) + 2.29 | 200:1 | 100 + 0.5 | 57 | 19 |
| (I-3) + 2.29 | 200:1 | 100 + 0.5 | 48 | 43 |
| (I-1) + 2.1 | 100:1 | 100 + 1 | 62 | 27 |
| (I-3) + 2.1 | 100:1 | 100 + 1 | 88 | 49 |
| (I-1) + 2.27 | 25:1 | 100 + 4 | 98 | 85 |
| (I-3) + 2.27 | 25:1 | 100 + 4 | 98 | 89 |
| (I-1) + 2.6 | 25:1 | 100 + 4 | 57 | 34 |
| (I-1) + 2.8 | 100:1 | 100 + 1 | 81 | 50 |
| (I-3) + 2.8 | 100:1 | 100 + 1 | 86 | 65 |
| (I-1) + 2.12 | 100:1 | 100 + 1 | 88 | 34 |
| (I-3) + 2.12 | 100:1 | 100 + 1 | 79 | 54 |
| (I-1) + 2.21 | 50:1 | 100 + 2 | 93 | 65 |
| (I-3) + 2.21 | 50:1 | 100 + 2 | 81 | 75 |

*found = activity found
**calc. = activity calculated using Colby's formula

TABLE 8

Sphaerotheca test (cucumbers)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 100 | 0 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 50 | 19 | |
| 2.2 | boscalid | 40 | 86 | |
| | | 20 | 62 | |
| 1.41 | prothioconazole | 2 | 19 | |
| (I-1) + 2.2 | 2.5:1 | 100 + 40 | 93 | 86 |
| (I-3) + 2.2 | 2.5:1 | 50 + 20 | 76 | 69 |
| (I-1) + 1.41 | 50:1 | 100 + 2 | 64 | 19 |

*found = activity found
**calc. = activity calculated using Colby's formula

TABLE 9

Sphaerotheca test (cucumbers)/preventive

|  | Active compounds |  | Application rate of active compound in ppm a.i. | Efficacy in % found* | calc.** |
|---|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | | 100 | 38 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | | 50 | 29 | |
| 5.5 | copper hydroxide | | 10 | 29 | |
| 5.8 | copper oxychloride | | 50 | 10 | |
| 5.25 | metiram | | 50 | 29 | |
| 10.10 | propamocarb HCl | | 400 | 0 | |
| | | | 200 | 0 | |
| 5.30 | sulphur | | 200 | 19 | |
| (I-3) + 5.5 | | 5:1 | 50 + 10 | 57 | 50 |
| (I-1) + 5.8 | | 2:1 | 100 + 50 | 76 | 44 |
| (I-3) + 5.25 | | 1:1 | 50 + 50 | 57 | 50 |
| (I-1) + 10.10 | | 1:4 | 100 + 400 | 57 | 38 |
| (I-3) + 10.10 | | 1:4 | 50 + 200 | 62 | 29 |
| (I-3) + 5.30 | | 1:4 | 50 + 200 | 57 | 42 |

*found = activity found
**calc. = activity calculated using Colby's formula

EXAMPLE 4

Venturia test (apples)/preventive
Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (Venturia inaequalis) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE 10

Venturia test (apples)/preventive

|  | Active compounds |  | Application rate of active compound in ppm a.i. | Efficacy in % found* | calc.** |
|---|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | | 100 | 0 | |
| | | | 50 | 0 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | | 100 | 0 | |
| | | | 50 | 0 | |
| 2.1 | bixafen | | 1 | 84 | |
| 2.27 | N-[1-(2,4-dichlorophenyl)-1-methoxypropan-2-yl]-3-(difluoromethyl)-1-methyl-1H-pyrazole-4-carboxamide | | 4 | 93 | |
| | | | 2 | 31 | |
| 2.6 | fluopyram | | 4 | 21 | |
| 2.8 | fluxapyroxad | | 0.5 | 25 | |
| 2.21 | penthiopyrad | | 2 | 8 | |
| (I-3) + 2.1 | | 100:1 | 100 + 1 | 90 | 84 |
| (I-1) + 2.27 | | 25:1 | 100 + 4 | 99 | 93 |
| (I-3) + 2.27 | | 25:1 | 50 + 2 | 83 | 31 |
| (I-1) + 2.6 | | 25:1 | 100 + 4 | 56 | 21 |
| (I-1) + 2.8 | | 100:1 | 50 + 0.5 | 84 | 25 |

TABLE 10-continued

Venturia test (apples)/preventive

| Active compounds | Application rate of active compound in ppm a.i. | Efficacy in % found* | calc.** |
|---|---|---|---|---|
| (I-3) + 2.8 | 100:1 | 50 + 0.5 | 90 | 25 |
| (I-1) + 2.21 | 50:1 | 100 + 2 | 100 | 8 |
| (I-3) + 2.21 | 50:1 | 100 + 2 | 68 | 8 |

*found = activity found
**calc. = activity calculated using Colby's formula

TABLE 11

Venturia test (apples)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 100 | 13 | |
| | | 50 | 4 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 100 | 15 | |
| | | 50 | 0 | |
| 3.3 | azoxystrobin | 0.25 | 38 | |
| 2.2 | boscalid | 20 | 85 | |
| 3.12 | fluoxastrobin | 0.5 | 44 | |
| 3.17 | pyraclostrobin | 0.5 | 19 | |
| 1.47 | tebuconazole | 2 | 11 | |
| 3.22 | trifloxystrobin | 0.5 | 77 | |
| (I-1) + 3.3 | 200:1 | 50 + 0.25 | 64 | 40 |
| (I-3) + 3.3 | 200:1 | 50 + 0.25 | 46 | 38 |
| (I-1) + 2.2 | 2.5:1 | 50 + 20 | 95 | 86 |
| (I-1) + 3.12 | 200:1 | 100 + 0.5 | 59 | 51 |
| (I-3) + 3.12 | 200:1 | 100 + 0.5 | 84 | 52 |
| (I-1) + 3.17 | 200:1 | 100 + 0.5 | 54 | 30 |
| (I-3) + 3.17 | 200:1 | 100 + 0.5 | 89 | 31 |
| (I-3) + 1.47 | 50:1 | 100 + 2 | 44 | 24 |
| (I-1) + 3.22 | 200:1 | 100 + 0.5 | 100 | 80 |
| (I-3) + 3.22 | 200:1 | 100 + 0.5 | 100 | 80 |

*found = activity found
**calc. = activity calculated using Colby's formula

TABLE 12

Venturia test (apples)/preventive

| | Active compounds | Application rate of active compound in ppm a.i. | Efficacy in % found* | calc.** |
|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | 100 | 21 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | 100 | 0 | |
| 15.60 | 2,6-dimethyl-1H,5H-[1,4]dithiino[2,3-c:5,6-c']di-pyrrole-1,3,5,7(2H,6H)-tetrone | 50 | 24 | |
| 5.4 | chlorothalonil | 20 | 14 | |
| (I-1) + 15.60 | 2:1 | 100 + 50 | 66 | 40 |
| (I-3) + 15.60 | 2:1 | 100 + 50 | 56 | 24 |

TABLE 12-continued

Venturia test (apples)/preventive

| Active compounds | | Application rate of active compound in ppm a.i. | Efficacy in % found* | calc.** |
|---|---|---|---|---|
| (I-1) + 5.4 | 5:1 | 100 + 20 | 74 | 32 |
| (I-3) + 5.4 | 5:1 | 100 + 20 | 91 | 14 |

*found = activity found
**calc. = activity calculated using Colby's formula

TABLE 13

Venturia test (apples)/preventive

| | Active compounds | | Application rate of active compound in ppm a.i. | Efficacy in % found* | calc.** |
|---|---|---|---|---|---|
| (I-1) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate | | 100 | 0 | |
| (I-3) | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate | | 100 | 0 | |
| 5.5 | copper hydroxide | | 20 | 25 | |
| 5.8 | copper oxychloride | | 50 | 8 | |
| 5.25 | metiram | | 100 | 55 | |
| 5.30 | sulphur | | 400 | 11 | |
| (I-1) + 5.5 | | 5:1 | 100 + 20 | 56 | 25 |
| (I-3) + 5.5 | | 5:1 | 100 + 20 | 50 | 25 |
| (I-1) + 5.8 | | 2:1 | 100 + 50 | 50 | 8 |
| (I-3) + 5.8 | | 2:1 | 100 + 50 | 60 | 8 |
| (I-1) + 5.25 | | 1:1 | 100 + 100 | 82 | 55 |
| (I-3) + 5.25 | | 1:1 | 100 + 100 | 73 | 55 |
| (I-1) + 5.30 | | 1:4 | 100 + 400 | 99 | 11 |
| (I-3) + 5.30 | | 1:4 | 100 + 400 | 98 | 11 |

*found = activity found
**calc. = activity calculated using Colby's formula

The invention claimed is:

1. A composition comprising:
(A) (I-3) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate
and/or an agrochemically acceptable salt thereof,
and
(B) a further active compound which is
(15.24) fosetyl aluminium,
wherein A and B are present in a weight ratio A:B of 1:1 to 1:1,000.

2. A composition for controlling phytopathogenic harmful fungi, comprising a content of at least one composition according to claim 1, in addition to one or more extenders and/or surfactants.

3. A composition according to claim 2 comprising at least one further active ingredient selected from the group of the insecticides, attractants, sterilants, bactericides, acaricides, nematicides, fungicides, growth regulators, herbicides, fertilizers, safeners and semiochemicals.

4. A plant growth regulator composition comprising the composition according to claim 1.

5. The composition according to claim 1, wherein A and B are present in a weight ratio of A:B of 1:1 to 1:100.

6. The composition according to claim 1, wherein A and B are present in a weight ratio of A:B in of 1:1 to 1:500.

7. The composition according to claim 1, wherein A and B are present in a weight ratio of A:B of 1:5 to 1:1000.

8. The composition according to claim 1, wherein the composition is synergistically effective and the only active compounds present are A and B.

9. A method for controlling phytopathogenic harmful fungi, comprising applying a composition according to claim 1 to phytopathogenic harmful fungi and/or a habitat thereof.

10. A method according to claim 9 comprising treating one or more transgenic plants.

11. A method according to claim 9 comprising treating seed and/or seed of a transgenic plant.

12. A process for producing a composition for controlling phytopathogenic harmful fungi, comprising mixing a composition according to claim 1 with one or more extenders and/or surfactants.

* * * * *